(12) United States Patent
Litvay

(10) Patent No.: US 7,491,195 B2
(45) Date of Patent: Feb. 17, 2009

(54) PERFORMANCE INDEX FOR ABSORBENT ARTICLES HAVING IMPROVED LEAKAGE PERFORMANCE

(75) Inventor: John D. Litvay, Downingtown, PA (US)

(73) Assignee: First Quality Retail Services LLC, Great Neck, NY (US)

( * ) Notice: Subject to any disclaimer, the term of this patent is extended or adjusted under 35 U.S.C. 154(b) by 301 days.

(21) Appl. No.: 10/673,638

(22) Filed: Sep. 30, 2003

(65) Prior Publication Data

US 2005/0043697 A1   Feb. 24, 2005

(51) Int. Cl.
  *A61F 13/15* (2006.01)
(52) U.S. Cl. .............................. 604/385.101; 604/378; 604/385.28
(58) Field of Classification Search .......... 604/385.101, 604/378, 385.28
See application file for complete search history.

(56) References Cited

U.S. PATENT DOCUMENTS

| | | | |
|---|---|---|---|
| 2,940,133 A | 6/1960 | Heritage | |
| 3,061,878 A | 11/1962 | Chapman | |
| 4,050,462 A | 9/1977 | Woon et al. | |
| 4,300,562 A | 11/1981 | Pieniak | |
| 4,834,735 A * | 5/1989 | Alemany et al. | 604/368 |
| 5,092,861 A | 3/1992 | Nomura et al. | |
| 5,281,207 A | 1/1994 | Chmielewski et al. | |
| 5,683,809 A | 11/1997 | Freeman et al. | |
| 5,749,863 A | 5/1998 | Payne | |
| 5,817,079 A | 10/1998 | Bergquist et al. | |
| 5,853,402 A | 12/1998 | Faulks et al. | |
| 5,863,288 A | 1/1999 | Baker | |
| 5,941,864 A | 8/1999 | Roe | |
| 5,957,906 A | 9/1999 | Roe et al. | |
| 6,017,336 A | 1/2000 | Sauer | |
| 6,040,251 A | 3/2000 | Caldwell | |
| 6,068,620 A | 5/2000 | Chmielewski | |
| 6,107,539 A | 8/2000 | Palumbo et al. | |
| 6,114,596 A | 9/2000 | Nayak et al. | |
| 6,117,121 A | 9/2000 | Faulks et al. | |
| 6,867,346 B1 * | 3/2005 | Dopps et al. | 604/378 |

* cited by examiner

Primary Examiner—Jacqueline F. Stephens
(74) Attorney, Agent, or Firm—Amster, Rothstein & Ebenstein LLP

(57) ABSTRACT

An absorbent article is disclosed that provides improved leakage protection. Also disclosed are methods for using and preparing absorbent articles having improved leakage protection, methods for designing articles having improved leakage protection, and methods of measuring and determining the performance index of an absorbent article. The absorbent article having improved leakage protection has a 3 variable urine only leakage performance index ($PI_{3UL}$) of less than about 3.0, the $PI_{3UL}$ being determined in accordance with the following equation (1):

$$PI_{3UL} = 0.046(Tc) - 2.94(MS100) - 0.772(AUL) \qquad (1)$$

where Tc is the total capacity in grams, MS100 is the percent utilization of the core upon insult with 100 ml of 0.9 wt % saline solution, and AUL is the front pad absorbency under load, expressed in grams of 0.9 wt % saline solution absorbed per gram of pad material.

65 Claims, 21 Drawing Sheets

PERFORMANCE INDEX FOR ABSORBENT ARTICLES HAVING IMPROVED LEAKAGE PERFORMANCE

BACKGROUND OF THE INVENTION

1. Field of the Invention

This invention relates to the field of absorbent articles in general, and more particularly to absorbent articles that provide improved leakage protection. The invention also relates to methods for using and preparing absorbent articles having improved leakage protection, methods for designing articles having improved leakage protection, and methods of measuring and determining the performance index of an absorbent article.

2. Description of Related Art

Disposable absorbent articles typically include a moisture-impervious backing sheet, an absorbent pad, and a moisture permeable liner sheet (e.g., top sheet) that contacts the body of a person wearing the article. In addition, elasticized regions are provided around the edges of the article to secure the article about the waist and legs of a wearer. Diapers typically further comprise opposed front and rear waist portions defining a waist opening, a crotch portion disposed there between, and a pair of elastically contractible leg openings along the side edges of the crotch portion. Disposable diapers having elasticized margins for placement about the legs of a wearer are disclosed in U.S. Pat. No. 4,050,462 and U.S. Pat. No. 5,092,861. An absorbent article having elasticized side margins and waist band margins are shown in U.S. Pat. No. 4,300,562. These elasticized portions of the garment typically are designed to contain body exudates and hence, prevent leakage.

Despite previous advancements in the field of absorbent articles, the art continuously strives to produce more comfortable garments that are better able to contain urinary and fecal excretions. For instance, problems with prior diaper designs include leakage of urinary or fecal material from the garment. Prolonged contact of liquid or semi-solid excreta with the skin of the wearer also is a continuing problem in the art because the moisture vapor and heat generated by the body exudates trapped within a diaper may lead to conditions adjacent to the wearer's skin that promote skin irritation, infection, and the like. Although the top sheet, as described above, is generally effective in allowing the passage of bodily exudates outwardly, the moisture permeable nature of top sheets may result in leakage of liquids. Various approaches have been attempted to address the lateral leakage of liquids from absorbent articles.

For example, U.S. Pat. No. 6,114,596 discloses a breathable diaper, feminine hygiene, or like disposable sanitary product having a cloth-like outer surface and including a plurality of materials from the skin-facing side outwardly, a selectively-permeable top sheet, a core, an optional barrier, and a back sheet. The disclosed optional barrier is formed from a multi-layer non-woven material that is hydrophobic and vapor-permeable for limiting the outward escape of liquid there through while enabling the outward escape of heat and water vapor there through. The disclosed barrier has a base disposed adjacent the core outer surface. The disclosed back sheet is formed of a multi-layer non-woven material that is hydrophobic and vapor permeable for limiting the outward escape of liquid there through while enabling the outward escape of heat and water vapor there through. This back sheet is disclosed as being disposed at least partially as an outer surface of the diaper.

U.S. Pat. No. 6,017,336 discloses an absorbent article that includes a pair of compression resistant containment barriers that are configured to inhibit the lateral flow of fecal exudates along the surface of the absorbent article. The containment barriers are disclosed as being laterally spaced apart to provide a void space between the wearer's back side and the surface of the absorbent article for containing body exudates. The absorbent article is disclosed as optionally including a containment dam that is located on the body facing surface of the absorbent article and is configured to inhibit a longitudinal flow of fecal exudates along the surface of the absorbent article.

U.S. Pat. No. 5,597,906 discloses an absorbent article comprising a liquid pervious top sheet, a liquid pervious back sheet joined to at least a portion of the top sheet, an absorbent core disposed between at least a portion of the top sheet and the back sheet, and a waste management element disposed in at least a portion of the crotch region. The waste management element preferably has an acceptance under pressure value of greater than about 0.50 grams of a viscous fluid bodily waste per square inch of the waste management element. The waste management element also is disclosed as having a storage under pressure value of at least about 0.70 grams of the viscous fluid bodily waste per square inch of the waste management element. The waste management element also is disclosed as optionally having an Immobilization Under Compressed Inversion value of greater than about 70% of the viscous fluid bodily waste accepted by the waste management element. The waste management element is disclosed as being located anywhere in the article, including the crotch region.

U.S. Pat. No. 5,941,864 discloses a disposable absorbent article, such as a diaper having a first top sheet with apertures large enough for low-viscosity fecal material to pass through to a fecal material storage element. The fecal material storage element is disclosed as immobilizing the fecal material in position for dewatering, so that the liquid components of the fecal material are absorbed by the core and solid components of the fecal material are separated from the liquid components, to provide for easier cleaning of the wearer when the soiled disposable absorbent article is removed.

U.S. Pat. No. 6,040,251 discloses barrier webs having certain desirable physical qualities such as water resistance, increased durability, improved barrier qualities, and the like. Barrier webs are disclosed as comprising a web that has been treated with a curable shear thinned thixotropic polymer composition that is adapted to be substantially impermeable to liquids, permeable to gases and impermeable to microorganisms. Further, the barrier webs are disclosed as being either impermeable to all microorganisms or impermeable to microorganisms of certain sizes. Also disclosed are fabrics that are capable of either selectively binding certain microorganisms, particles, or molecules depending upon what binding partners are incorporated into the polymer before application to the fabric.

U.S. Pat. No. 6,117,121 discloses an absorbent article including an absorbent core located between a body-side liner and an outer cover. The absorbent article is disclosed as having a leg cuff mounted to a base structure in the crotch portion thereof. The leg cuffs are disclosed as being partially stretched when attached to respective longitudinal side portions near the crotch portion of the absorbent article.

U.S. Pat. No. 6,107,539 discloses disposable absorbent articles comprising a back sheet, a top sheet, a fluid acquisition/distribution region and at least one fluid storage region, the article having a total product acquisition performance of more than 3.75 ml/sec in the first gush and more than 0.5 ml/sec in the fourth gush and an in bag stack height of less than 9.9 mm. The article is characterized in that the top sheet allows it to retain no more then 0.25 g of fluid as measured by the top sheet-on-acquisition-material-wetness test, and that the acquisition/distribution region has a drip capacity of at least 5.0 grams of fluid per gram of material.

U.S. Pat. No. 5,683,809 discloses protective articles such as diapers, having film-less hydrophobic barrier elements such as cuffs and backing sheets. The barrier cuffs—which can be, for instance, leg cuffs and waistbands—and the backing sheets can be provided from fabrics having a fabric weight of at least 10 g/y$^2$.

U.S. Pat. No. 5,817,079 discloses absorbent products, such as sanitary napkins, discreet areas of dry fibrous materials such as fluid-repellent materials are precisely placed in various planes within the product so as to provide barriers to bodily fluid leakage from the product. In a preferred embodiment, hydrophobic fibers are placed around the periphery of a central absorbent area of an absorbent product to discourage and/or prevent side or end leakage from the product.

As is apparent from the foregoing, there are a variety of mechanisms for controlling leakage in absorbent garments. However, all of these proposed means are deficient in terms of effectiveness and low product quality, mechanical complexity in design, and/or associated cost inefficiencies.

The description herein of the various known products, methods, and apparatus and their attendant disadvantages is in no way intended to limit the scope of the present invention, or to imply that the present invention does not include some or all of the various elements of the products, methods, and apparatus in one form or another. Indeed, various embodiments of the invention may be capable of overcoming some of the disadvantages noted herein, while still retaining some or all of the various elements of the known products, methods, and apparatus in one form or another.

All documents described herein are incorporated by reference in this disclosure in their entirety.

SUMMARY OF THE INVENTION

It therefore is desirable to provide cost-efficient absorbent articles that display superior leak protection, as well as methods of designing and making such absorbent articles. It also is desirable to provide a method of predicting leakage performance based on absorbent garment variables, and to methods of enhancing the leakage performance (e.g., reducing leakage) by modifying one or more of these variables. It also is desirable to develop an indicator of leakage performance, such as a performance index, which assists in the design of an absorbent article having improved leakage performance.

In accordance with features of various embodiments of the present invention, there is provided an absorbent article that includes a top sheet, a back sheet, and an absorbent core disposed at least partially between the top sheet and the back sheet. The absorbent article has a 3 variable urine only leakage performance index ($PI_{3UL}$) of less than about 3.0, whereby the $PI_{3UL}$ is determined in accordance with the following equation (1):

$$PI_{3UL}=0.046(Tc)-2.94(MS100)-0.772(AUL) \quad (1)$$

where Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein.

Another embodiment of the invention encompasses an absorbent article that has a five variable urine only leakage Performance Index ($PI_{5UL}$) of less than about negative 6.4, whereby $PI_{5UL}$ is determined in accordance with the following equation (2):

$$PI_{5UL}=0.006(Tc)-7.094(Se)+1.108(MS100)-0.18(AUL)+0.023(St) \quad (2)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein.

Yet another embodiment of the invention includes an absorbent article having a 3 variable overall leakage performance index ($PI_{3OL}$) of less than about negative 2.65, whereby the $PI_{3OL}$ is determined in accordance with the following equation (3):

$$PI_{3OL}=0.062(Tc)-17.54(MS100)-1.107(AUL) \quad (3)$$

where Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein.

An additional feature of an embodiment of the invention encompasses an absorbent article that has a five variable overall leakage Performance Index ($PI_{5OL}$) of less than about negative 9.3, whereby $PI_{5OL}$ is determined in accordance with the following equation (4):

$$PI_{5OL}=0.018(Tc)-3.75(Se)-11.35(MS100)-0.465(AUL)+0.033(St) \quad (4)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein.

In accordance with another feature of an embodiment of the invention, there is provided a method of designing an absorbent article to have reduced urine only leakage comprising modifying one or more absorbent article variables by carrying out one or more procedures selected from: (i) increasing the front pad absorbency under load (AUL) to a value of about 23 grams of fluid/gram of material or more; (ii) increasing the percent utilization of the absorbent core (MS100) to a value of about 43% or more; (iii) increasing the surrounds efficiency (Se) to a value of about 90% or more; (iv) decreasing the third void strikethrough (St) to a value of less than about 30 seconds; and (v) maintaining the total capacity of the absorbent article (Tc) to a value of less than about 495 grams and greater than about 465. It is preferred in the present invention that more than one of the above variables is modified as described.

In accordance with yet another embodiment of the invention, there is provided a method of designing an absorbent article to have reduced overall leakage comprising modifying one or more absorbent article variables by carrying out one or more procedures selected from: (i) increasing the front pad absorbency under load (AUL) to a value of about 23 grams of fluid/gram of material or more; (ii) increasing the percent utilization of the absorbent core (MS100) to a value of about 43% or more; (iii) increasing the surrounds efficiency (Se) to a value of about 89% or more; (iv) decreasing the third void strikethrough (St) to a value of less than about 38 seconds; and (v) maintaining the total capacity of the absorbent article (Tc) to a value of less than about 495 grams and more than about 465 grams. It is preferred in the present invention that more than one of the above variables is modified as described.

In accordance with yet another feature of an embodiment of the invention, there is provided a method of making an absorbent article that includes providing a top sheet, a back sheet, and an absorbent core to a garment forming station. The method further includes disposing the absorbent core at least partially between the top sheet and the back sheet at the garment forming station. In accordance with the method, the absorbent article is produced such that it has a three variable urine only leakage performance index of less than about 3.0. Other methods include producing the absorbent article so that it has a $PI_{5UL}$ of less than about −6.4, a $PI_{3OL}$ of les than about −2.65, or a $PI_{5OL}$ of less than about −9.3.

Another feature of various embodiments of the present invention includes a method of determining the three variable urine only leakage performance index of an absorbent article that includes measuring at least the total capacity, the front pad AUL and the percent utilization of the absorbent article. The method also optionally includes measuring the surrounds efficiency and the third void strikethrough of the absorbent article. The method concludes by calculating the performance index of the article by carrying out the following calculation (1):

$$PI_{3UL}=0.046(Tc)-2.94(MS100)-0.772(AUL) \qquad (1)$$

The method also can encompass a method of determining the five variable urine only leakage Performance Index by determining the absorbent article variables described above, and then calculating the Performance Index in accordance with the following equation 2:

$$PI_{5UL}=0.006(Tc)-7.094(Se)+1.108(MS100)-0.18(AUL)+0.023(St) \qquad (2)$$

Another feature of an embodiment of the invention includes a method of designing an absorbent article having reduced leakage that includes first measuring a plurality of variables on a plurality of different absorbent articles. The method also includes determining the percentage of the plurality of absorbent articles that leak (urine only or overall leakage percentage) through actual use tests, and then determining which of the plurality of variables for the plurality of absorbent articles provides a substantially direct correlation with the leakage percentage (urine only or overall) to produce at least one leakage variable that directly correlates with leakage percentage. The method then includes adjusting at least one of the at least one leakage variable to reduce the leakage percentage of the absorbent article.

These and other features of various embodiments of the invention will be readily apparent from a review of the detailed description of preferred embodiments taken in conjunction with the attached drawings.

DETAILED DESCRIPTION OF PREFERRED EMBODIMENTS

Figure 1:
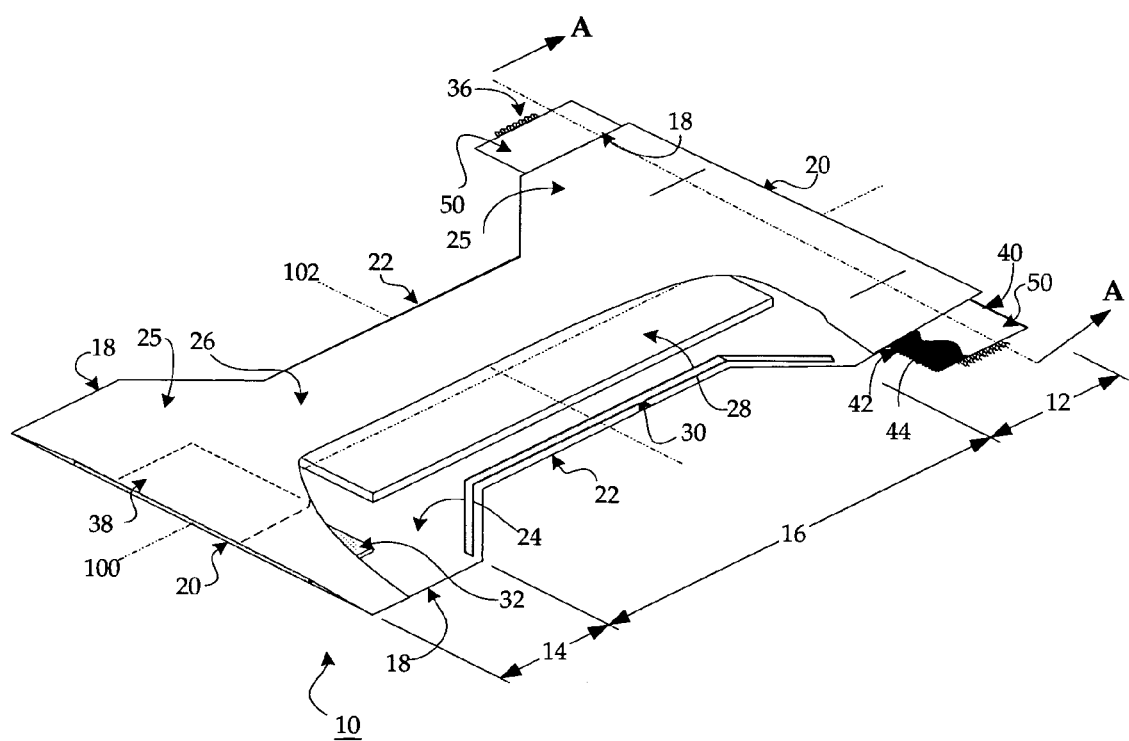
FIG. 1 is an exploded view of an absorbent article of a preferred embodiment of the invention, with the effects of elastics removed for clarity.

As used herein, the terms "absorbent garment," "absorbent article" or simply "article" or "garment" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. Some of the embodiments described herein provide, as an exemplary structure, a diaper for an infant, however this is not intended to limit the claimed invention. The invention will be understood to encompass, without limitation, all classes and types of absorbent garments, including those described herein. Preferably, the absorbent composite is thin in order to improve the comfort and appearance of a garment.

Throughout this description, the expressions "upper layer," "lower layer," "above" and "below," which refer to the various components included in the absorbent composite and absorbent core embodiments of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core may be folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, a transfer layer, a fluid handling layer, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow.

Throughout this description, the expression "outer layers" relates in general to an upper layer and a lower layer in spatial relation to the central absorbent layer, but can include additional layers that may be present. The upper layer and lower layer preferably are made from tissue, however, other materials such as latex or thermally bonded airlaid fluff pulp, (e.g., roll good available from Walkisoft, Merfin or Georgia Pacific), or synthetic spunbonded, carded, or hydro-entangled non-woven materials may be used as the upper and lower layers, or may be added as additional layers.

Throughout this description, the expression "absorbent core" relates to an absorbent core that is used in the manufacture of absorbent garments. Throughout this description, the expression "superabsorbent material" relates generally to a material that can imbibe, absorb or gel about 10 times its own weight of fluid and retain it under moderate pressure, wherein the fluid is taken into the molecular structure and not simply contained in pores from which it could be expressed by squeezing. Throughout this description, the expression "superabsorbent polymer" (SAP) relates generally to a type of superabsorbent material that comprises a polymer.

Throughout this description the expression "Performance Index" denotes an indicator of leakage developed in accordance with the present invention and is based on a number of absorbent article variables. The various Performance Indices developed by the present inventors are excellent predictors of leakage, as determined through actual use tests. Two types of leakage are observed in actual use tests: (i) urine only leakage, which typically is the more prevalent and most important in designing an absorbent article; and (ii) overall leakage. Thus, a three variable urine only Performance Index ($PI_{3UL}$) is an index developed using three absorbent article variables, and denotes a predictor of urine only leakage. The lower the Performance Index, the better the leakage.

The present invention relates in general to an absorbent article having improved leakage protection. Improved leakage in the context of the invention denotes less leakage, when compared to conventional or control absorbent garments. In the context of the present invention, the absorbent garments have a 3 variable urine only leakage performance index ($PI_{3UL}$) of less than about 3.0, whereby the $PI_{3UL}$ is determined in accordance with the following equation (1):

$$PI_{3UL}=0.046(Tc)-2.94(MS100)-0.772(AUL) \quad (1)$$

where Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein. It is most preferred that the absorbent article be a Stage 4 diaper, because this is believed to be the most popular diaper size. Stage 4 diapers typically are used for infants weighing anywhere from about 20 to about 40 pounds.

It is preferred that the absorbent articles have a $PI_{3UL}$ of less than about 2.9, more preferably, less than about 2.75, and most preferably less than about 2.70. The lower limit for $PI_{3UL}$ preferably is about 0.5, and more preferably about 0.6, and most preferably about 0.75. A value for the Performance Index that is too low may indicate a total capacity that is too low, which is undesirable in the context of the present invention.

The present invention also includes absorbent articles that have a five variable urine only leakage Performance Index ($PI_{5UL}$) of less than about negative 6.4, whereby $PI_{5UL}$ is determined in accordance with the following equation (2):

$$PI_{5UL}=0.006(Tc)-7.094(Se)+1.108(MS100)-0.18(AUL)+0.023(St) \quad (2)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein. It is most preferred that the absorbent article be a Stage 4 diaper, because this is believed to be the most popular diaper size.

It is preferred that $PI_{5UL}$ be less than about negative 6.5, more preferably less than about negative 6.6, and most preferably less than about negative 6.75. The lower limit for $PI_{5UL}$ preferably is about negative 9.3, preferably about negative 9.1, and most preferably about negative 8.75. A value for the Performance Index that is too low may indicate a total capacity that is too low, or a percent utilization that is too low, which are undesirable in the context of the present invention.

The present invention also includes absorbent articles that have a 3 variable overall leakage performance index ($PI_{3OL}$) of less than about negative 2.65, whereby the $PI_{3OL}$ is determined in accordance with the following equation (3):

$$PI_{3OL}=0.062(Tc)-17.54(MS100)-1.107(AUL) \quad (3)$$

where Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein. It is most preferred that the absorbent article be a Stage 4 diaper, because this is believed to be the most popular diaper size.

It is preferred that the absorbent articles have a $PI_{3OL}$ of less than about negative 2.75, more preferably, less than about negative 2.85, and most preferably less than about negative 2.9. The lower limit for $PI_{3OL}$ preferably is about negative 7.0, and more preferably about negative 6.5, and most preferably about negative 6.3. A value for the Performance Index that is too low may indicate a total capacity that is too low, which is undesirable in the context of the present invention.

The present invention also includes absorbent articles that have a five variable overall leakage Performance Index ($PI_{5OL}$) of less than about negative 9.3, whereby $PI_{5OL}$ is determined in accordance with the following equation (4):

$$PI_{5OL}=0.018(Tc)-3.75(Se)-11.35(MS100)-0.465(AUL)+0.033(St) \quad (4)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, each of which is determined in accordance with the procedures outlined herein. It is most preferred that the absorbent article be a Stage 4 diaper, because this is believed to be the most popular diaper size.

It is preferred that $PI_{5OL}$ be less than about negative 9.45, more preferably less than about negative 9.6, and most preferably less than about negative 9.75. The lower limit for $PI_{5UL}$ preferably is about negative 13.0, preferably about negative 12.5, and most preferably about negative 12.35. A value for the Performance Index that is too low may indicate a total capacity that is too low, or a percent utilization that is too low, or a third void strikethrough that is too high, each of which is undesirable in the context of the present invention The present invention also relates to methods of making absorbent garments that have the requisite Performance Index, methods of determining the Performance Index, methods of designing absorbent garments using the Performance Index, and methods of designing absorbent garments by determining the relationships between a variety of physical properties of the garment and leakage, and then modifying or altering one or more of the properties that are found to have a direct relationship to leakage.

The present invention is premised in part on the notion that leakage in an absorbent article is primarily affected by at least three variables, and preferably about five variables. The Performance index therefore is a function of these three variables, and more preferably five variables:

$$PI=f(Tc,\text{pad }AUL,MS100) \quad (5);$$

and more preferably, $$PI=f(Tc,\text{pad}AUL,SE,\text{Strikethrough},MS100) \quad (6),$$

where Tc is the total capacity, pad AUL is the front pad absorbency under load of the absorbent article, Se is surrounds efficiency, Strikethrough is the third void strikethrough, and MS100 is the percent utilization of the core upon insult with 100 ml of 0.9 wt % saline solution. The methods by which each of these variables is determined are described in more detail in the testing methods section below.

These relationships were developed by the present inventor by measuring a variety of physical properties of a variety of absorbent garments, determining the amount of leakage of the garments, either experimentally or through user testing, (urine only and overall leakage), and then determining which of the physical properties had a direct relationship with leakage. The physical properties that were found to have a direct relationship with leakage using conventional regression analyses then were modeled using statistical analysis to determine the overall effect the select physical properties had on urine only, and overall absorbent garment leakage. The Performance Index is a numerical index that can be assigned to this overall effect, and can be used as an indicator for product leakage. Thus, an absorbent garment with a lower Performance Index is believed to be more resistant to leakage, using the physical properties designated herein.

The particular methodology used in the present invention can be used to generate a Performance Index for any type of absorbent material. The particular equations and linear regressions set forth in this description pertain to an absorbent garment, and preferably a diaper, and more preferably a stage 4 diaper. Those skilled in the art recognize, however, that the invention is not limited to the particular absorbent garments described herein, but could be used on any absorbent material, diaper, or size of diaper.

An initial determination typically is made to establish what physical properties will be measured. This determination can be made by taking into consideration any number of a variety of factors. For example, for leakage, one typically would seek to measure those physical properties of an absorbent garment that are most likely to have an effect on leakage, either through experience, or through the available literature. Various physical properties such as basis weight, thickness, the type of superabsorbent polymer and the type of fiber used, both of which can be measured using the front pad AUL test, the capacity, the effects of the leg gathers and standing leg gathers on preventing egress of body exudates, etc., can be determined for a variety of absorbent garments, and then regressed against actual and experimental leakage results.

The absorbent garment of the present invention can be any absorbent garment now known or later discovered. For explanation purposes only, however, the invention will be described with reference to a particularly preferred absorbent garment; an infant's diaper. The invention now will be described with reference to the attached drawings illustrating preferred embodiments of the invention. For clarity, features that appear in more than one Figure have the same reference number in each Figure.

FIG. 1 is a partially cut away depiction of an exemplary embodiment of an absorbent garment 10 (preferably a disposable absorbent garment) of the present invention. The embodiment shown in FIG. 1 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the back and front of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 form the perimeter of a pair of leg openings, when the garment 10 is placed on a subject wearer.

The garment 10 preferably comprises a top sheet 24, and a back sheet 26, which may be substantially coterminous with the top sheet 24. When the garment 10 is being worn, the top sheet 24 faces the wearer's body, and the back sheet 26 faces away from the wearer. An absorbent core 28 preferably is disposed between at least a portion of the top sheet 24 the back sheet 26.

An embodiment of the present invention may further comprise various additional features. One or more pairs of elastic gathers 30 may extend adjacent the crotch edges 22. The garment 10 may also comprise one or more waste containment systems, such as inboard standing leg gathers 40, which preferably extend from the second waist region 14 to the first waist region 12 along opposite sides of longitudinal center line 100 (only one standing leg gather 40, or waist containment flap 40 is shown in FIG. 1 for clarity). One or both of the first and second waist regions 12, 14 may also be equipped with strips of elastic waist foam 32 or other elastically extensible material, which help contract the garment around the wearer's waist, providing improved fit and leakage prevention.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise an elastically extensible material 44, and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. The invention is not intended to be limited to any specific materials for these components, other than those that are capable of achieving the desired Performance Index. For example, it is preferred to use a top sheet 24 that has excellent strikethrough properties (e.g., acquires fluid rapidly). The top sheet 24 and back sheet can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

Due to the wide variety of backing and liner sheet construction and materials currently available, the invention is not intended to be limited to any specific materials or constructions of these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02-0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite of different sheet materials, chemical treatment, heat treatment, or other processes or methods known in the art. Some regions of the back sheet 26 may be fluid pervious.

In one embodiment of the invention, the back sheet 26 is fluid impervious in the crotch 16, but is fluid pervious in portions of the first and second waist regions 12, 14. The back sheet 26 may also be made from a multi-layer of overlaid sheets of material.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent core 28. Examples of suitable liner sheet materials include non-woven spun bond or carded webs of polypropylene, polyethylene, nylon, polyester and blends of these materials.

The back sheet 26 may be covered with, or laminated to, or be comprised of a laminate together with a fibrous, non woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded non woven web of synthetic fibers such as polypropylene, polyethylene or polyester fibers; a non woven web of cellulosic fibers, textile fibers such as rayon fibers, cotton and the like, or a blend of cellulosic and textile fibers; a spun-bonded non woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent core 28 while outboard non-woven breathable side back sheet panels are attached to the side edges of the central poly back sheet panel. Alternatively, the back sheet 26 may be formed from microporous poly coverstock for added breathability.

The top sheet 24 may be formed of three separate portions or panels. Those skilled in the art will recognize, however, that top sheet 24 need not be made of three separate panels, and that it may be comprised of one unitary item. A first central top sheet panel may comprise a central top sheet panel formed from preferably a liquid-pervious material that is either hydrophobic or hydrophilic. The central top sheet panel may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel is a cover stock of single ply non-woven material which may be made of carded fibers, either adhesively or thermally bonded, perforated plastic film, spun bonded fibers, or water entangled fibers, which generally weigh from 0.3-0.7 oz./sq. yd. and have appropriate and effective machine direction and cross-machine direction strength suitable for use as a baby diaper cover stock material. The central top sheet panel preferably extends from substantially the second waist region 14 to the first waist region 12, or a portion thereof. The first top sheet panel also may fully envelop the absorbent core 28, such that the second and third top sheet panels are disposed laterally away from the lateral edges of the absorbent core 28.

The second and third top sheet panels (e.g., outer top sheet panels), in this alternative embodiment may be positioned laterally outside of the central top sheet panel. The outer top sheet panels preferably are substantially liquid-impervious and hydrophobic, preferably at least in the crotch area. The outer edges of the outer top sheet panels may substantially follow the corresponding outer perimeter of the back sheet 26. The material for the outer top sheet portions or panels is preferably polypropylene and can be woven, non-woven, spun bonded, carded or the like, depending on the application.

The second and third top sheet panels preferably are designed to extend upwardly to form the waste containment flaps 40. The waste containment flaps 40 preferably are formed of the same material as the outer top sheet portions or panels.

The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner. In this alternative embodiment, the central top sheet portion or panel may extend past the connection point with the waste containment flaps 40, and even extend to the periphery of the back sheet 26.

The waste containment flaps 40 preferably include a portion that folds over onto itself to form a small enclosure. At least one, and depending on the size of the enclosure sometimes more than one, elastic member may be secured in the enclosure in a stretched condition. As is well known in the art, when the flap elastic attempts to assume the relaxed, unstretched condition, the waste containment flaps 40 rises above the surface of the central top sheet portion or panel (e.g., extends orthogonal to the plane of formed by longitudinal and lateral centerlines 100, 102.

The top sheet 24 may be made of any suitable relatively liquid-pervious material currently known in the art or later discovered that permits passage of a liquid there through. Examples of suitable top sheet materials include non woven spun-bonded or carded webs of polypropylene, polyethylene, nylon, polyester and blends of these materials, perforated, apertured, or reticulated films, and the like. Non woven materials are exemplary because such materials readily allow the passage of liquids to the underlying absorbent core 28. The top sheet 24 preferably comprises a single-ply non woven material that may be made of carded fibers, either adhesively or thermally bonded, spun bonded fibers, or water entangled fibers, which generally weigh from 0.3-0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make second and third top sheet panels, preferably are substantially fluid impervious and hydrophobic, while the remainder of the top sheet 24 (e.g., central top sheet panel) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a multi-layer of overlaid sheets of material. The top sheet 24 also may be treated in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent core 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, the absorbent garment 10 preferably is provided with leg elastics 30 extending through crotch region 16, adjacent crotch edge 22. The absorbent garment 10 of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics 32 may preferably comprise foam strips positioned at the first and second waist regions 12, 14, respectively. Such foam strips preferably are about ½ to about 1½ inches wide and about 3-6 inches long. The foam strips preferably are positioned between the top sheet portions 24 or panels and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are stretched 50-150%, preferably 100% more than their unstretched dimension before being secured between the back sheet 26 and top sheet 24.

Each edge 22 that forms the leg openings preferably is provided with an adjacent leg elastic containment system 30. In the preferred embodiment, three strands of elastic threads are positioned to extend adjacent to leg openings between the outer top sheet 24 and the back sheet 26. Any suitable elastomeric material exhibiting at least an elongation (defined herein as $(L_S-L_R)/L_R$ where $L_S$ is the stretch length of an elastic element and $L_R$ is retracted length, multiplied by 100 to obtain percent elongation) in the range of 5%-350%, preferably in the range of 200%-300%, can be employed for the leg elastics 30. The leg elastics 30 may be attached to the absorbent article 10 in any of several ways which are known in the art. For example, the leg elastics 30 may be ultrasonically bonded, heat/pressure sealed using a variety of bonding patterns, or glued to the garment 10. Various commercially available materials can be used for the leg elastics 30, such as natural rubber, butyl rubber or other synthetic rubber, urethane, elastomeric materials such as LYCRA (DuPont), GLOSPAN (Globe) or SYSTEM 7000 (Fulflex).

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a reinforcement patch below the front waist portion so that the diaper may be checked for soiling without compromising the ability to reuse the fastener. Alternatively, other absorbent article fastening systems are also possible, including safety pins, buttons, and snaps.

As stated previously, the invention has been described in connection with a diaper. The invention, however, is not intended to be limited to application only in diapers. Specifically, the absorbent composites of the preferred embodiments may be readily adapted for use in other absorbent garments besides diapers, including, but not limited to, training pants, feminine hygiene products and adult incontinence products.

The underlying structure beneath the top sheet 24 may include, depending on the diaper construction, various combinations of elements, but in each embodiment, it is contemplated that the absorbent garment 10 will preferably include an absorbent core 28. In addition, additional layers may be disposed between the top sheet 24 and absorbent core 28, or between the absorbent core 28 and back sheet 26. An additional layer also may be included in the absorbent core 28. The additional layer(s) may include a fluid transfer layer, a fluid handling layer, a storage layer, a wicking layer, a fluid distribution layer, and any other layer(s) known to those having ordinary skill in the art.

Although the absorbent core 28 depicted in FIG. 1 has a substantially rectangular cross-sectional and plan view shape, other shapes may be used, such as a "T" shape or an hourglass shape. The shape of the absorbent core 28 may be selected to provide the greatest absorbency with a reduced amount of material. The absorbent core may be associated with the top sheet 24, back sheet 26, or any other suitable part of the garment 10 by any method known in the art, in order to fix the absorbent core 28 in place. In addition to the respective layers in the absorbent core 28, as will be described in greater detail hereinafter, the overall absorbent core 28 may be enclosed within a tissue wrapping, as disclosed in U.S. Pat. No. 6,068,620, the disclosure of which is incorporated by reference herein in its entirety. Skilled artisans are capable of designing and wrapping a suitable absorbent core 28 of the invention, using the guidelines provided herein.

In a preferred embodiment, the absorbent core 28 comprises super absorbent polymer distributed within a fibrous structure. Absorbent cores 28 of this type generally are known in the art, and exemplary absorbent cores are described in U.S. Pat. Nos. 6,068,620 and 5,281,207, both issued to Chmielewski, and U.S. Pat. No. 5,863,288, issued to Baker, the disclosures of each of which are herein incorporated by reference in their entirety and in a manner consistent with this disclosure.

The fibrous component of the absorbent core 28 may be any fibrous material now known or later discovered. Suitable fibrous materials include fluff pulp, soft and hard Kraft woods, and the like. The fibrous component preferably is comprised of a continuous fiber, and most preferably is a crimped tow of cellulose acetate or polyester. Before making the absorbent composite that includes a continuous fiber, the continuous fiber typically is unwound and opened, and then cut at various lengths to provide a fibrous mass of material. Skilled artisans are aware of techniques available to open continuous fibers and form the opened fibers into a fibrous mass.

In addition to the continuous fiber material used as the fibrous component in absorbent core 28, other fibrous components also may be used. For example, additional continuous fibers (different from the original continuous fiber), or a low-density roll good made in a separate process may be used.

Still further yet, the fibrous component could also be a carded web formed on-line. Optionally, it is advantageous to introduce from about 1-5% of a thermally bondable fiber into the fibrous component of the absorbent core 28 for wet strength and core stability in use.

Any superabsorbent polymer (SAP) now known or later discovered may be used in absorbent core 28. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility. Examples of suitable SAP are water swellable polymers of water soluble acrylic or vinyl monomers crosslinked with a polyfunctional reactant. Also included are starch modified polyacrylic acids and hydrolyzed polyacrylonitrile and their alkali metal salts.

Any SAP now known or later discovered can be used in the absorbent core 28 of the invention. Commercially available SAPs include a starch modified superabsorbent polymer available under the trade name SANWET® or HYSORB® from BASF Corporation, Portsmouth, Va. SANWET® is a starch grafted polyacrylate sodium salt. Other commercially available SAPs include a superabsorbent derived from polypropenoic acid, available under the tradename DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARID-ALL 1125 manufactured by Chemdall Corporation; FAVOR manufactured by Stockhausen Inc.; AQUA KEEP SA60S, manufactured by Seitetsu Kagaku Co., Ltd.; DIAWET, commercially available from Mitsubishi Chemicals, Japan; FLOSORB, available from SNF Floerger, France, AQUALIC, available from Nippon Shokubai, Osaka, Japan.

The SAP may be provided in any particle size, and suitable particle sizes vary greatly depending on the ultimate properties desired. For example, a fine particulate rather than a coarse particulate may be used in the invention, and preferably a fine particulate that passes through an about 200 mesh screen may be used. The SAP can be a foam SAP or an in-situ SAP whereby monomer particles are sprayed onto a web (e.g., a non-woven web) of material and then polymerized, or any other type of SAP now known or later developed.

The absorbent core 28 may be surrounded by a liquid pervious tissue over-wrap, or other material, which may be treated to be hydrophobic or hydrophilic, or to have other properties. The absorbent core 28, and any tissue wrap enclosing it, may be folded, crimped, thermally bonded, or otherwise manipulated to provide additional benefits. It is envisioned that a variety of folding patterns may be employed to provide additional fluid handling capabilities. For example, the absorbent core 28 may be folded into a U shape, a C shape, a G shape, a Z shape, or other shapes, as viewed along the longitudinal axis 100, to provide fluid handling channels, multiple layers of absorbent material, or other benefits. Folded absorbent cores are discussed, for example, in U.S. Pat. No. 6,068,620.

It generally is known that the type of SAP, as well as the type of fibrous material used in absorbent core 28, play a role in the overall absorbency of the absorbent garment. Indeed, the present inventor has found that the front pad absorbency, expressed herein as front pad AUL, and determined in accordance with the testing protocol described herein, is directly related to leakage of the absorbent garment. Accordingly, the Performance Index of the absorbent garment can be modified to improve the garment's leakage prevention by enhancing the absorbency. Various methods of enhancing the absorbency can be used. For example, using more SAP, or using a SAP having higher absorbency characteristics (e.g., higher AUL), changing the density, size, and shape of the core, increase wicking, add layers (wicking layer, transfer layer, etc.), can be employed to improve the Performance Index. Using the guidelines provided herein, those skilled in the art will be capable of designing a suitable absorbent core 28 for use in an absorbent garment 10 having the Performance Index characteristics described herein.

The total basis weights of the absorbent composite 28 including fibrous materials, SAP, tissue, additional layers, and additives, are anywhere from about 100-600 grams per square meter. The most preferred total basis weight of the absorbent composite 28 is from about 250 to about 350 grams per square meter. It is preferred that when a tow fiber is used, the total basis weight of the absorbent composite is within the range of from about 20 to about 300 g per square meter, and most preferably from about 100 to 150 grams per square meter. Optionally, about 1-10%, preferably about 5%, by weight of thermally bondable synthetic fibers can be added to the absorbent composite 28 to impart additional wet strength to the composite. This will improve the stability of the core during use of the diaper. The preferred synthetic fibers are polyolefin/polyester fibers and polyester/polyester bicomponent fibers.

An embodiment of the invention encompasses designing an absorbent garment to have less leakage by measuring a plurality of physical properties of a plurality of absorbent garments, whereby the physical properties are those that are believed most likely to have an affect on leakage. While not intending on being bound by any theory of operation, the inventor believes that the following physical properties of an absorbent garment may play a role in leakage: mass, basis weight, front pad absorbency ("AUL"), total capacity (Tc), Strikethrough, percent utilization of the absorbent garment, ability to retain body exudates (surrounds efficiency), vertical wicking, density, and tissue capacity. Upon reading the test methods described below, and the remainder of this description, it will be readily apparent to those skilled in the art what features of the absorbent garment have the greatest impact on the various properties described above. Accordingly, those skilled in the art will be capable of modifying any or all of these features to improve the leakage characteristics, and hence improve the Performance Index of the absorbent garment, using the guidelines provided herein.

For example, the type and amount of SAP used in the absorbent core 28 is a significant contributor to the front pad absorbency. The type of top sheet material 24, and the use of a fluid acquisition layer, are features that affect the Strikethrough. The percent utilization of the garment is affected by the distribution of the SAP throughout the absorbent core 28, as well as the ability of the top sheet, acquisition layer and core materials to adequately "wick" the body exudates throughout the core surface area. The number and type of elastic materials used in leg gathers 30, and standing leg gathers 40 (or waist containment flaps) may affect the surrounds efficiency. Other features that may affect the surrounds efficiency include the height of the leg gathers, the density of the core, the phobicity of the material used, etc. These and other product variables readily apparent to those skilled in the art can be modified to improve the leakage characteristics of an absorbent article.

The following test methods are those used to measure the physical properties that play a role in leakage:

Test Methods

Diaper Mean Weight

The purpose of this test was to measure the mean weight of the diaper.

About 100 diapers were selected from the sample population. Diapers were selected evenly throughout the population. For example, if the population consisted of eight bags of diapers, 12 diapers were chosen from each of 4 bags and 13 diapers were chosen from each of the remaining 4 bags.

A digital balance was used to measure the mean weight, and the balance was first "zeroed" to ensure the value of zero on the balance before beginning the procedure. The first diaper then was placed on the balance, and the weight measured and recorded after the balance was stabilized. The diaper was removed from the balance, and the procedure repeated for the total of the diapers selected, neatly stacking the diapers in sets of ten after measuring their weights. After the weights were recorded and written on the final diaper, the mean weight and standard deviation for all of the diapers were calculated. Only those diapers that fell within ± one standard deviation of the mean weight were selected for the testing described below, unless otherwise indicated (e.g., select a diaper having a high mean weight or a low mean weight).

Basis Weight and Density

Figure 2:
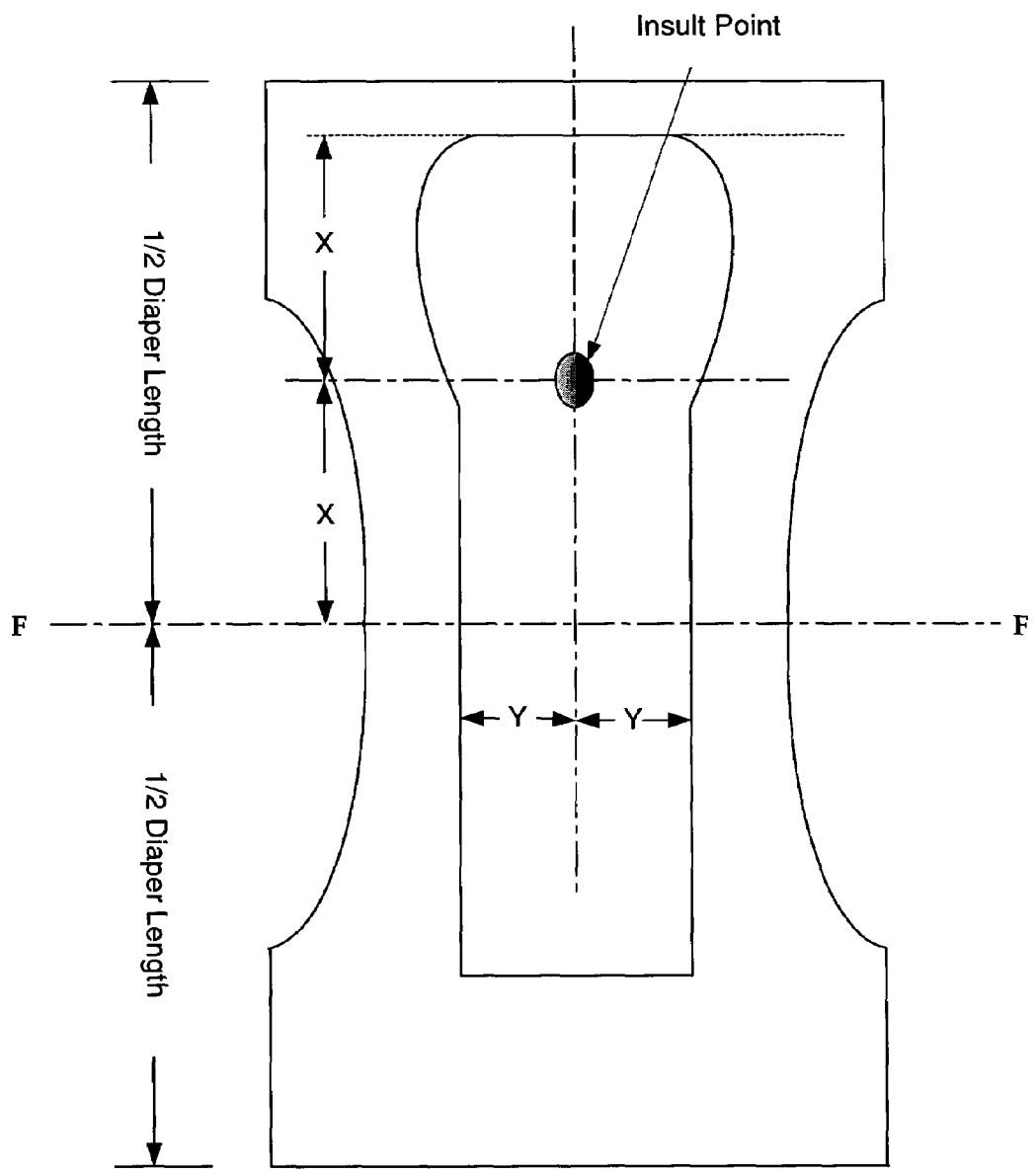
FIG. 2 is a top view of the insult point of an absorbent article.

Approximately 10 mean weight diapers were selected, ensuring that the diapers were free of wrinkles, creases, or lumps. The sample area at the insult point was determined as shown in FIG. 2, the diaper was cut in half at the crotch, and the half containing the insult point was maintained. A rectangle surrounding the insult point where the sample will be cut was marked. A die-cutter having an area of 1/300 square meters (50 millimeters×66.7 millimeters) was used to cut the sample.

A caliper having L and W model 51D20 type SPEC manufactured by AB Lorentzen and Wettre, Stockholm, Sweden, with a pressure foot area of 25 square centimeters and a Mitutoyo precision digital indicator was used to measure the basis weight and density. The caliper was set to zero by pressing the "zero" button, so that the display read 0.00 mm. The pressure foot of the caliper was raised by pressing the button on the side of the caliper to raise the pressure foot high enough to place the sample in the gap. The area under the pressure foot was marked. The button then was released to allow the pressure foot to lower onto the sample.

At the first indication that the reading on the thickness gauge was slowing down, the timer was started and set for 30 seconds. At the first sound of the timer alarm, the thickness of the sample was recorded. The sample was released from the caliper, and the sample cut with the die cutter on the marked location. The balance then was "tared" so that the display read 0.00 g. The sample was placed on the balance and weighed.

The basis weight was calculated in accordance with equation (7) below:

$$\text{Basis Weight} = \text{Sample Weight}(g) \times 300(1/m^2) = g/m^2 \quad (7).$$

The density was calculated in accordance with equation (8) below:

$$\text{Density} = \text{Basis Weight}(g/m^2)/\text{Thickness}(mm)/1000 = g/cc \quad (8).$$

Front to Back Basis Weight Ratio

The following equipment was used to measure and calculate the front to back basis weight ratio: a digital balance with at least 100 gram capacity and at least 0.01 gram resolution; a caliper having L and W base with a pressure foot area of 25 square centimeters and a Mitutoyo precision digital indicator; a die-cutter (1/300 square meters—50 millimeters×66.7 millimeters); scissors; and a timer or stopwatch.

Figure 3:
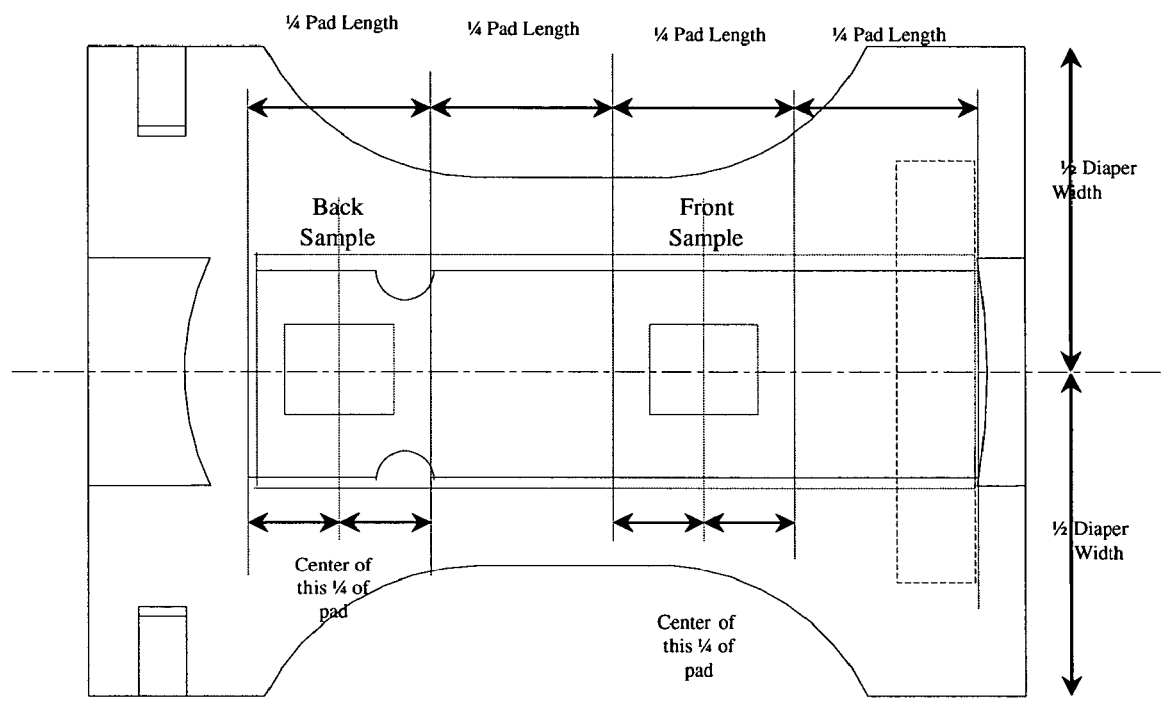
FIG. 3 is a top view of an absorbent article showing the loci where the front pad AUL is determined.

Approximately 6 mean weight diapers were selected that were free of wrinkles, creases, or lumps. A rectangle in the front and back of the diapers were marked as shown in FIG. 3, which indicated where the samples were to be cut. The respective samples were labeled to indicate their sample number and location. The diapers then were cut in half between the front and back samples.

The timer was set for 30 seconds, and the caliper was zeroed by pressing the "ZERO" button on the caliper until the display read 0.00 millimeters. The pressure foot was raised high enough to place the sample in the measuring gap, and the sample labeled "front" was placed under the foot. The pressure foot then was lowered onto the sample, and at the first indication that the reading on the thickness gauge was slowing down, the timer was started. At the first sound of the timer alarm, the thickness of the sample was recorded to the nearest 0.01 millimeters, and the sample was released. This procedure was repeated for the sample labeled "back."

The sample labeled "front" then was cut with the die-cutter, the digital balance was tared by pressing the "TARE" bar on the balance so that the display read 0.00 grams. The sample was placed on the balance, and the weight recorded to the nearest 0.01 grams. The sample labeled "back" then was cut and weighed in the same manner as the sample labeled "front."

The front basis weight, back basis weight, front density, back density, and front to back basis weight ratio then were calculated using the equations and sample calculations below.

$$\text{Diaper Basis Weight}(g/m^2) = \text{Sample Weight}(g) \times 300(1/m^2) \quad (7)$$

$$\text{Diaper Density }(g/cm^3) = \frac{\text{Diaper Basis Weight }(g/m^2)}{\text{Caliper}(mm) \times 1000} \quad (8)$$

$$\text{Front to Back BW Ratio} = \frac{\text{Front Basis Weight }(g/m^2)}{\text{Back Basis Weight }(g/m^2)} \quad (9)$$

Vertical Wicking of Tissue Used to Make Absorbent Core

Figure 4:
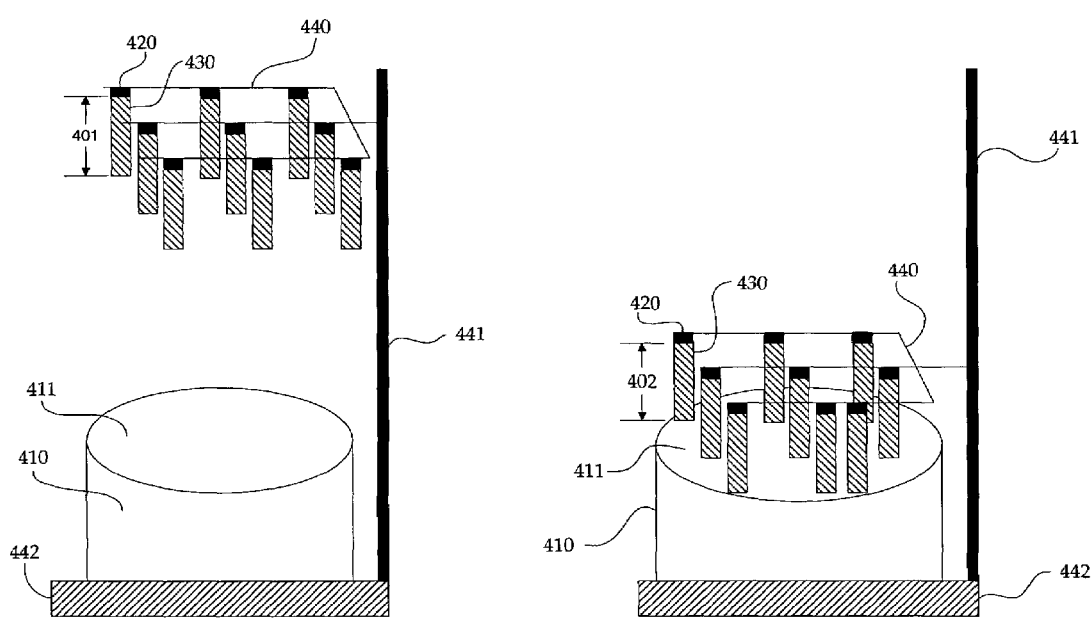
FIG. 4 is a schematic of an apparatus useful in performing the vertical wicking and tissue capacity tests described herein.

Sample Preparation: Samples for the vertical wicking test were prepared by choosing tissue samples 430 (FIG. 4) that were not damaged and were free of any foreign matter such as oil or dye. If the tissues needed to be extracted from a diaper, they were gently removed without damaging the sample. The tissue then was cut into a 1×8 inch sample 430 (52 cm$^2$) and one end labeled with permanent marker. On the same end as labeled, a mark was measured and placed 8 mm from the edge. This is where the sample 430 will be clamped so that the sample has a resulting length 401 of about 19.5 cm. (8 in.−8 mm=19.5 cm).

Solution Preparation: Approximately 45(g) of sodium chloride crystals were weighed in a dry weighing dish, and then added along with de-ionized water to a clean dry 5000 ml flask stopping at the 5000 ml mark. The concentration of the saline solution was measured with a refractometer to insure 0.9% concentration of saline. About 10 drops of blue food coloring solution then were added to assist in viewing the solution during the test, and the solution 411 was poured into a large beaker 410.

Test Method: A stand including a base 442, column 441, and a three row attachment 440 with clamps 420 was placed above the large beaker 410 filled with the solution 411, with the large beaker 410 resting on the base 442, and the three row attachment 440 with samples 430 disposed above and out of the solution 411. The solution 411 was prepared to be at least 10 cm deep. The clamps 420 then were flipped or the attachment 440 raised to avoid submersion while clamping the samples 430, until all the samples 430 were in a position and ready for testing. On the three row attachment 440, the samples 430 were hung without hanging more than 3 to 4 samples on one row to avoid crowding. Each sample 430 was clamped at the 8 mm mark on the labeled end, so that about 19.5 cm of the sample hung freely from each claim 420.

Each sample was hung freely, and the three row attachment 440 lowered into the solution bath 411 so that the bottom 5 mm of each sample was submersed in the solution 411. The resulting exposed length 402 of the sample 430 was therefore about 19 cm. A timer was started simultaneously as the samples were submersed. The samples remained submersed for about 1 minute, at which time the clamps 420 were flipped, or the three row attachment 440 raised to lift the samples 430 from the solution bath 411. The absorptive level then was marked on each sample 430, the absorptive level being easily determined due to the blue color of solution 411. After recording the absorption level for each sample, the timer then was set for an additional 19 minutes and the samples 430 re-submerged in the solution 411. After the timer stopped (i.e., after 19 minutes had expired), the absorptive level on the sample 430 were again marked. The samples 430 were allowed to air dry and the 1 and 19 min. absorption levels were measured in centimeters.

Tissue Total Capacity Test

Sample and Solution Preparation: The sample 430 and solution preparation 411 was substantially the same as that described above for the vertical wicking test, with reference to FIG. 4.

Test Method: A stand 441 with clamps 420 was placed above the solution bath. Each 1×8 inch sample 430 was weighed in grams. The unwrinkled sample then was placed entirely in the solution bath, up to four at a time. The samples 430 were submerged with tweezers if necessary and each sample soaked for about 30 seconds. The samples 430 then were carefully removed from the solution 411 with tweezers, making sure to avoid wrinkling or tearing the samples 430. The samples 430 then were hung from the clamps 420 for one minute. While still hanging, the samples 430 were blotted with paper towel to remove excess solution. The wet samples then were weighed and the weight recorded. The total capacity value was the determined by subtracting the dry weight from the wet weight.

Diaper Total Capacity

The following equipment and reagants were used.

0.9% sodium chloride solution
Permanent marker
2 plastic tubs (approximately 8"deep×18"wide×24"long) or equivalent
Plastic basket to fit inside tub, approximately 1-2" tall
2 stainless steel weights, approximately 1150 g each
Plastic tray
Timer
Drain stand
Metal binder clips
Digital balance, with 100 g load and 0.1 g resolution
Platform balance, with 5000 g load and 2 g resolution
Plexiglas tray, dimensions larger than an open diaper Sample Preparation:

Approximately three diapers were selected; (i) one that was within one standard deviation of the mean weight for the diapers; (ii) one that was a high weight diaper; and (iii) one that was a low weight diaper. The diapers that were free of wrinkles, creases, lumps or bumps were selected. Each diaper was numbered on the back sheet 26 with a permanent marker.

Test Procedure:

Each diaper was weighed on the digital balance, and the weight recorded to the nearest 0.1 g. One tub was filled to about ¾ full with 0.9% saline. The first diaper was opened so that it lay flat with the top sheet 24 side facing up. This diaper was slowly placed in the tub of saline solution, such that the diaper was completely de-aerated. This procedure was repeated with the remaining diapers.

The plastic basket then was placed on top of the diapers and one or two weights were placed on the basket to keep the diapers submerged. The timer was started and set for 60 minutes (one hour). After one hour, the diapers were removed from the tub and placed into a second dry tub to pre-drain. Each diaper then was hung from its tab end off of the draining stand using two binder clips, and the timer again was started and set this time for ten minutes. After ten minutes had elapsed, the diapers were removed and placed on a dry plastic tray.

The dry plastic tray was carried to the balance, and the plexiglas tray was placed on the platform balance. The balance was "tared" so the weight measured 0.0, and then the first diaper was weighed and the weight recorded to the nearest gram. The remaining diapers were weighed, making sure each time to zero the balance before each new weight to account for any liquid that may have been left on the plexiglas from the previous diaper.

The total capacity of each diaper was calculated for each diaper, and the average taken for the three diaper samples. The total capacity was determined in accordance with equation (10) below:

$$\text{Capacity}(g) = \text{Wet diaper weight}(g) - \text{Dry diaper weight}(g) \quad (10)$$

Strikethrough and Rewet

The purpose of the Strikethrough and Rewet tests is to determine the strikethrough times, expressed in seconds, and the amount of rewet, expressed in grams, of a diaper. The strikethrough is a measure of how quickly the diaper can take up a given amount of fluid, and the rewet is a measure of how much liquid comes back out of a diaper when a 0.5 psi load is applied.

Figure 5:
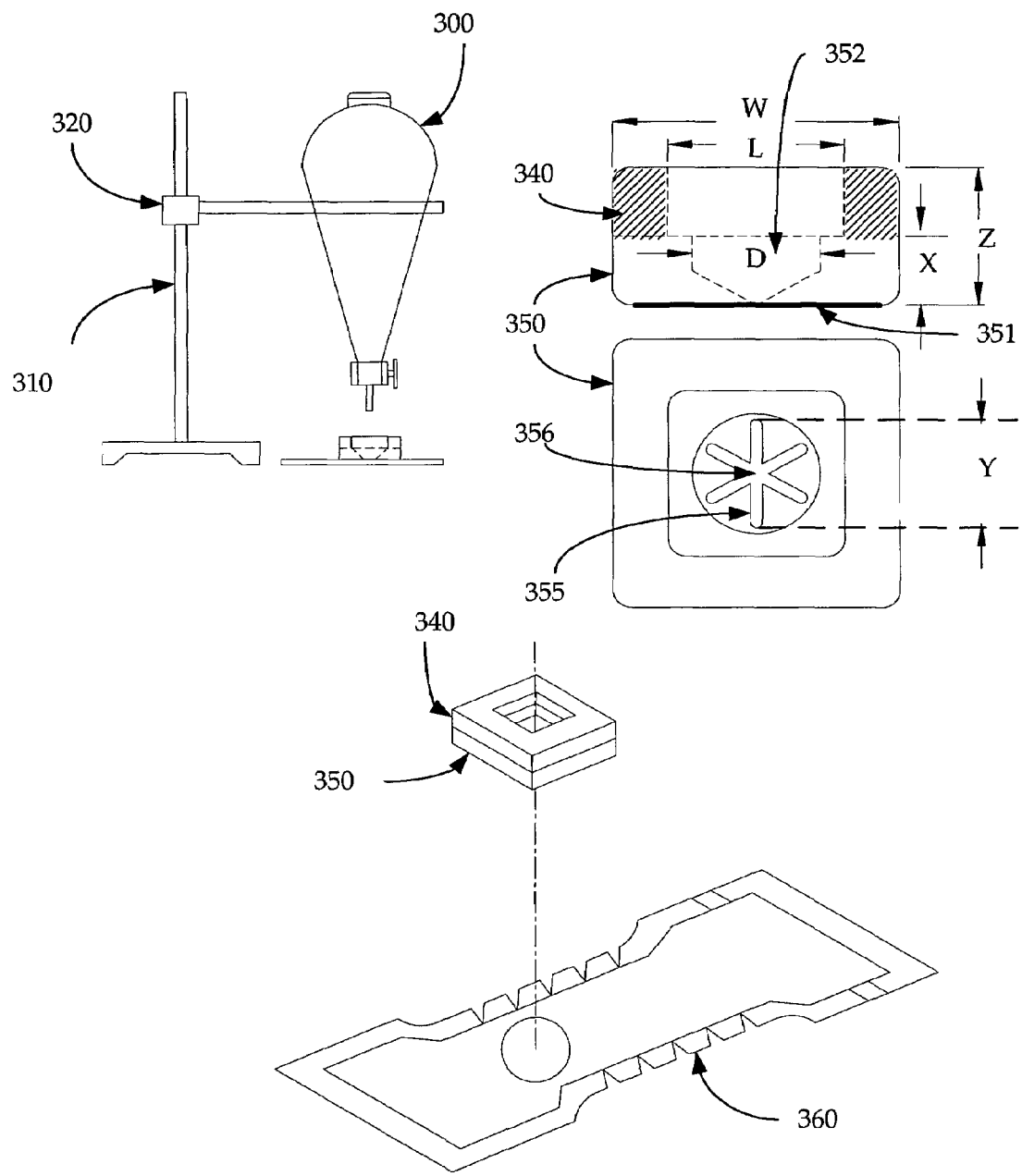
FIG. 5 is a schematic of apparatus useful in performing the Strikethrough and Rewet tests described herein.

The apparatus used to measure strikethrough and rewet generally is shown in FIG. 5. The materials used included a burette (not shown) with discharge valve, preferably a 250 ml burette, and a separatory funnel 300, preferably a 150 ml separatory funnel having a 6-7 ml/second stopcock. The apparatus further included a stand 310 with a clamp 320, and a strikethrough plate 350, which included a plexiglas cover plate 340 (4"×4"×¼"). Other materials used in the Strikethrough and Rewet test included a 0.5 psi weight (2.5"× 2.5"), Filter paper, Fisher Brand P8 filter paper cut to 4"×4", synthetic urine in the form of a 0.9% NaCl solution with 0.0025% Triton X-100 surfactant, a timer, a balance, and a stretch board with clamps 360.

As shown in FIG. 5, the strikethrough plate has specifically designed parameters. The strikethrough plate used to measure the Strikethrough and Rewet properties of the diapers meets the requirements set forth in edana Liquid Strike-Through Time Section 150.4-99, February 1999. Specifically, the strikethrough plate was constructed of a transparent acrylic sheet about 20 mm thick, which was placed on top of the strikethrough plate, having a thickness of about 17.8 mm. The strikethrough plate was fitted with corrosion-resistant electrodes 351 consisting of about 1.6 mm diameter platinum or stainless steel wire set in grooves of cross section of about 4.0 mm×7.0 mm cut into the base of the plate and fixed with quick-setting epoxy. The strikethrough plate 350 had an outlet opening at the top of the 17.8 mm deep bore 352, having a diameter D of a little more than about 25 mm. Thus, the values for X and D in FIG. 5 preferably are 17.8 mm, and 25 mm, respectively, although those skilled in the art will appreciate that the particular dimensions of D and X can vary. The bottom of the bore preferably had a center circular hub 356 with a diameter of about 1.9 mm with 6 symmetrically positioned spokes 355 extending about 11 mm from the hub. The value for Y in FIG. 5 therefore was about 22.225 mm, or about twice the length of each symmetrically positioned spoke 355. The slope of the bottom of bore 352 was about 25° from level.

The values for L, W, and Z in FIG. 5 also may vary, as will be appreciated by one of ordinary skill in the art. It was preferred that L be on the order of about 30 mm and W could be up to about 125 mm, but preferably was 70 mm. The overall thickness of the strikethrough plate, including strikethrough plate 350 and baseplate 340, designated by "Z" in FIG. 5, preferably was about 37.8 mm, whereby the baseplate 340 was about 20 mm thick.

The samples preferably were prepared for the Strikethrough and Rewet test by selecting 6 mean weight diapers, that were free of lumps, creases, and wrinkles. The diapers were weighed to the nearest 0.1 g. The insult point then was marked as shown in FIG. 2, which typically is positioned ½ the distance from the midpoint of the diaper to the end point of the absorbent core, whereby half the distance is indicated by the letter "X" in FIG. 2. The insult point also was at the midpoint of the width of the absorbent core, whereby half the width of the absorbent core is indicated by the letter "Y" in FIG. 2.

The synthetic urine was prepared by weighing approximately 5 g of Triton X-100 into a clean, 200 ml flask. Then, about 18 g NaCl was weighed and transferred into the same 200 ml flask container with the Triton X-100, and diluted with de-ionized water to 200 ml liter. The solution then preferably was stirred. The test solutions were discarded if not used within seven days, or if the percent saline was not about 0.9% by weight, as measured using a refractometer.

Strikethrough and Rewet then were tested in accordance with the following procedure.

The diaper was stretched onto a stretch board with clamps 360, making sure there were no bumps or wrinkles in the diaper (see, FIG. 3). Then, the insult point was marked on the diaper as shown in FIG. 2, and the strikethrough plate 350 was placed and centered on the insult point. Referring again to FIG. 5, the separatory funnel 300 was filled with 100 ml of test solution, and the tip of the separatory funnel 300 was centered a few mm above the strikethrough plate 350. The separatory funnel valve was opened and the timer started at the exact same time, keeping the cavity of the strikethrough plate 352 completely full with solution to maintain constant pressure. When the complete 100 ml solution had been absorbed into the diaper, the timer was stopped, and the Strikethrough value was recorded in seconds.

After recording the Strikethrough time, the plexiglas cover plate 340 was placed and centered on the insult point, and a 0.5 psi weight was placed onto the cover plate. The weight on the sample was left on the cover plate 340 for 10 minutes. Then, 18 g of filter paper was weighed and its weight recorded to the nearest 0.1 gram. After about 10 minutes had elapsed, the 0.5 psi weight was removed. The filter papers then were placed on the insult point, and the plexiglas cover plate 340 and the 0.5 psi weight were placed on top of filter papers. The cover plate and weight were left on the filter papers for 10 minutes. After 10 minutes has elapsed, the cover plate 340, the weight, and the filter papers were removed, and the weight of the wet filter papers was measured and recorded to the nearest 0.1 gram. This procedure from first striking the insult point with the 100 ml of solution, until the filter papers are weighed consists of an insult. Since this was the first time, it is denoted hereinafter as the first insult.

The procedure then was repeated on the same diaper sample for a second insult. For the second insult, however, about 50 grams of filter paper were used. The procedure then can be repeated on the same sample a third time for a third insult. For the third insult, however, about 72 grams of filter paper were used.

The Rewet was calculated by taking the difference in weight of the filter paper weighed before the plexiglas cover plate 340 and weight were placed thereon, and the filter paper weighed after ten minutes had elapsed with the plexiglas cover plate 340 and weight placed thereon, as shown in Equation (11) below. The Rewet values were designated as the first insult Rewet, second insult Rewet, and third insult Rewet, respectively. The Strikethrough value was the amount of time, in seconds, taken for 100 ml of solution to completely absorb into the diaper. The Strikethrough and Rewet values were taken for all six samples, and the values obtained represented the average for all six samples.

Rewet=Weight of wet filter paper−Weight of dry filter paper,(g)  (11)

Front Pad Total Absorptive Capacity Under Load

The Front Pad Total Absorptive Capacity Test Under Load (pad AUL) Method was used to measure the amount of a 1.0 weight % NaCl solution absorbed, on average, in ten (10) minutes by the front pad of a sample of an absorbent garment while the sample was subjected to a restraining pressure of 0.5 psi. The absorptive capacity under load was measured as gm of solution absorbed during ten (10) minutes of exposure to the solution under testing conditions.

A 1.0 weight % NaCl solution was prepared by weighing approximately 50 gm NaCl into a weighing dish, and then transferring the 50 gm NaCl to a 5000 ml container. The 5000 ml container was filled with deionized water and mixed to prepare a 1.0 weight % saline solution.

An absorbent article was selected as a sample to be tested. A circular sample approximately two (2) inches in diameter was removed from substantially in or around the insult point of the absorbent article. The insult point of the absorbent garment was determined by reference to FIG. 2, and as described in more detail earlier in this disclosure. The sample was cut from the absorbent article from the insult point using a two (2) inch diameter stainless steel metal circular die that was approximately 1⅝ inches high. Any cutting patterns may be used so long as the average total absorptive capacity of the front pad of the sample is measured. The samples were conditioned in a TAPPI room for at least 16 hours prior to testing. The TAPPI conditioned room was maintained at 72° F., 50% relative humidity.

Figure 6:
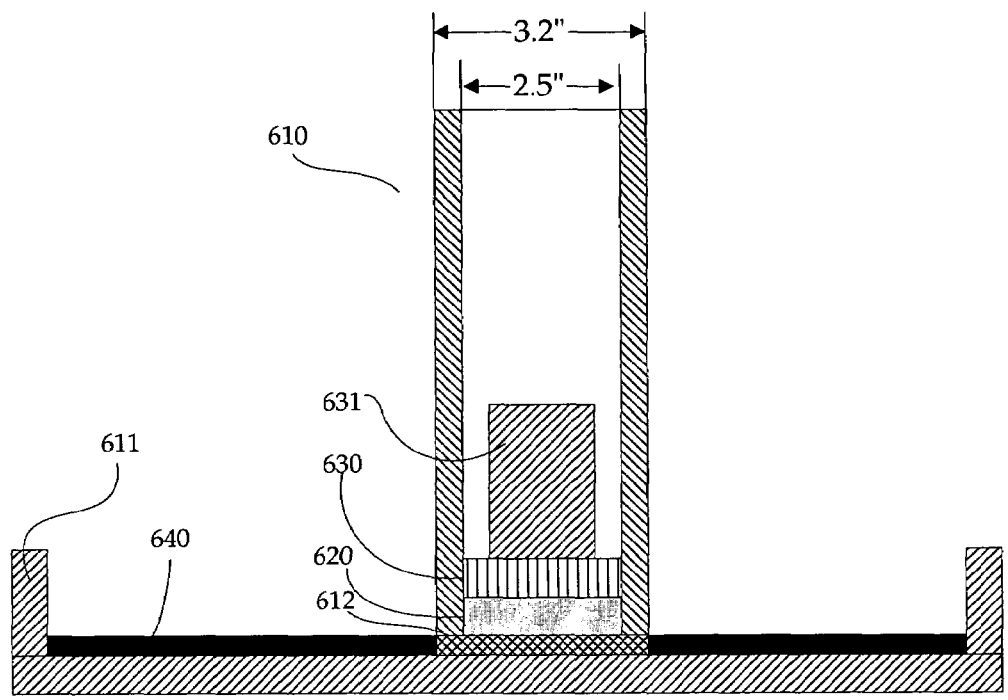
FIG. 6 is a schematic of an apparatus useful in performing the front pad AUL tests described herein.

The test utilized an apparatus 600 as shown in FIG. 6. The sample holder 610 was a cylindrical nylon basket, approximately three (3) inches outside diameter, with a cylindrical hole bored in the center of the sample holder that slightly exceeded the two (2) inches in diameter in order to accommodate the two (2) inch diameter sample 620. A 16 gauge stainless steel perforated plate 612 with ⅛ inch holes, and having an open area of approximately 40%, was placed at the bottom of the sample holder 610.

Each sample was weighed, then placed into a sample holder 610 with the top sheet facing downward toward the metal perforated plate 612. The weight of the filled sample holders 610 was measured. A load of approximately 0.5 psi was applied on top of each sample 620 in each filled sample holder 610 by placing a substantially two (2) inch in diameter cylindrical stainless steel weight 631 on top of a plexiglas plate 630, having substantially the same diameter, both of which were placed on top of sample 620. For a 0.5 psi load, the weight 631 was approximately 1¾ inches high. The weight 631 was machined to a size such that it closely approximated the cross sectional area of the sample 620 and yet may freely move up or down in the sample holder 610 during the test.

A sample box 611 was prepared for holding the filled sample holders 610. The sample box 611 was approximately ¼ inch thick plexiglass that was approximately 20 inches in width, 14½ inches in length, and 5 inches deep, and was water tight. Saline solution(0.9 wt %) 640 to cover the filled sample holders 610 was added to the sample box 611, which was approximately 120 ml more than the volume of saline solution required to rise ⅛ inch above the tops of the metal perforated plates 612 in the empty sample holders 610 when the empty sample holders 610 were placed into the sample box 611. The temperature was maintained at about 73.4° F. ±about 2° F.

The filled sample holders 610 were placed in the filled sample box 611 at substantially the same time. After ten (10) minutes, the filled sample holders 610 were removed from the sample box 611 and allowed to drip for one (1) minute. The weight 631 then was removed from the filled sample holders 610.

The filled sample holders then were weighed. The total absorptive capacity of each sample, in gm of solution absorbed, is the weight of solution absorbed by the sample during the ten (10) minute exposure to the 1.0 weight % saline solution while under a restraining pressure of 0.5 psi. The front pad total absorptive capacity under load (pad AUL) was calculated by determining the difference in the weight of the filled sample holder measured before and after the test. If multiple samples were taken from one absorbent garment, the average total absorptive capacity of the front pad was determined by averaging front pad total absorptive capacities.

Percent Utilization Test

The purpose of the percent utilization test was to determine the mass percent of a diaper core used under varying insult levels.

The following equipment and reagents were used in this test:
  500 ml burette with stopcock or 100 ml funnel
  plastic hose—attached to the end of the burette
  stand and clamps—to hold and stabilize burette
  sodium chloride crystals
  blue food coloring dye
  half baby mannequin with pipe inside
  tray
  de-ionized water
  stop watch
  25 ml Graduated Cylinder or Larger Beaker
  sharpie pen
  calibrated oven
  balance
  scissors Two (2) diapers were chosen that were a representation of the mean weight of the particular brand of diaper. Each diaper was labeled with it's dry weight and any other relevant information. A 0.9 wt % Saline solution without Triton-X was prepared as follows. Approximately 45 (g) of sodium chloride crystals were weighed in a dry weighing dish, and then added together with de-ionized water to a clean dry 5000 ml flask stopping at the 5000 ml mark. The concentration of the solution was measured with a refractometer to insure 0.9% concentration. About 10 drops of blue food coloring were added to add color to solution for easy viewing.

Figure 7:
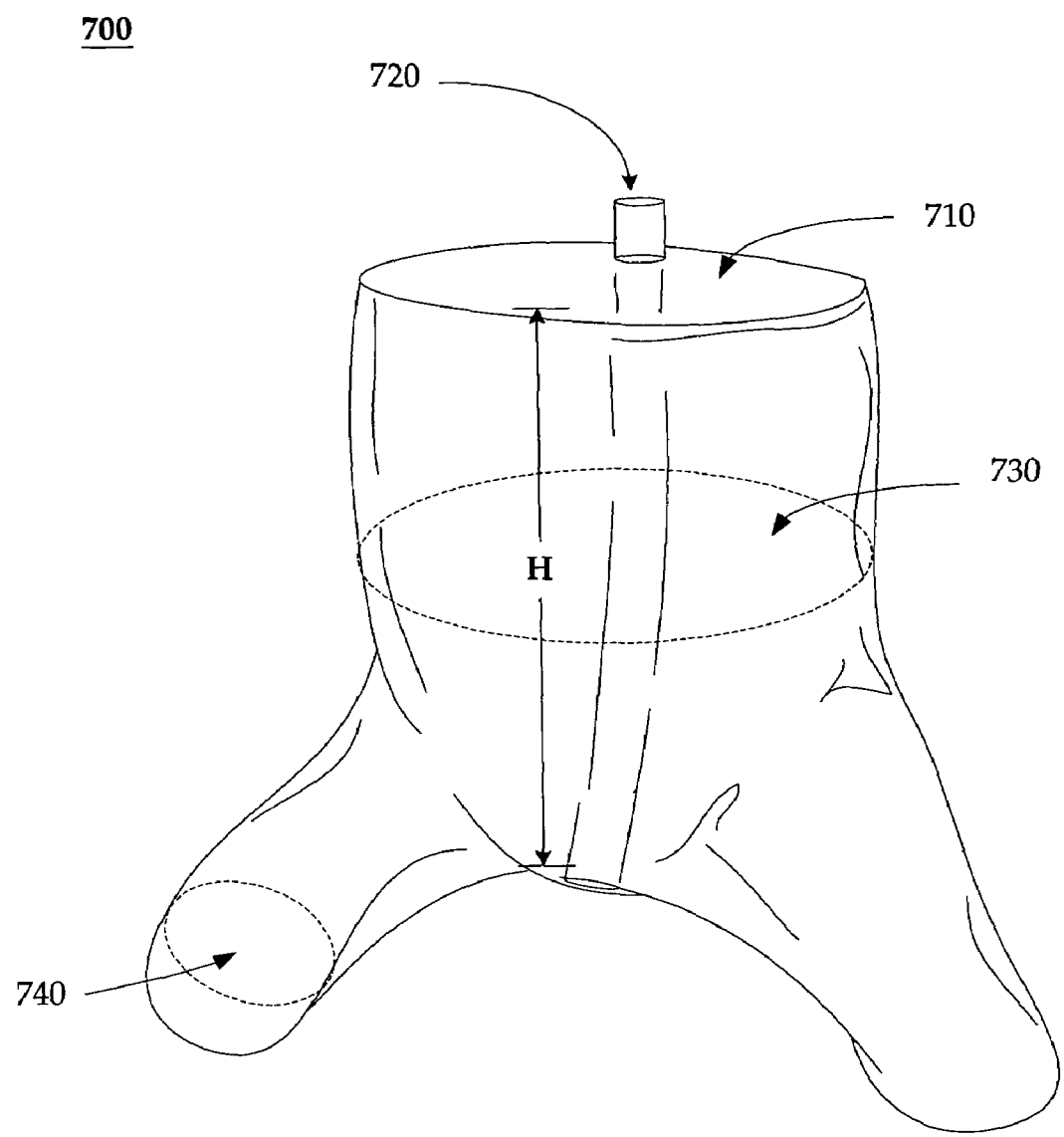
FIG. 7 is schematic of a mannequin used in the leakage tests described in more detail in the testing methods section below.

A sample diaper was opened and placed onto a mannequin 700 similar to that shown in FIG. 7 using the diaper closure system (hook and loop) or tape. The mannequin is a commercially available mannequin, available from Design Innovation, 20 Towerlane, Avon, Conn. 06001. The mannequin 700 shown in FIG. 7 is designed of a clear material (preferably a plexiglas or other clear plastic material) with a hole 720 extending from the waist portion down into the crotch area. The hole 720 has an outside diameter of about ⅝ inch, and an inside diameter of about ½ inch, and is connected to a mannequin pipe having a height "H" of about 7.5 inches. The legs of mannequin 700 preferably have a circumference 740 of about 7.5 inches.

The waist 730 of mannequin 700, which is where the diaper will be attached thereto using the fastening tabs 34 attached to target device 38, preferably has a circumference of about 16.25 inches. The upper circumference 710 of mannequin 700 preferably is about 17 inches. The hole 720 of mannequin 700 enables one to introduce a dyed saline solution into the crotch area to simulate an insult of a diaper. Leakage will occur when the colored saline solution is seen exiting the diaper.

A suitable fit for the diaper will have the standing leg gathers 40 standing up, the leg gathers 30 positioned outward (opposite diaper core), and the diaper core centered and placed close to the mannequin and around the crotch. To avoid diaper slippage, the diaper was taped to the waist area 730 near the top of the mannequin using masking tape.

Plastic tubing extending from the burette (not shown) into the top hole 720 of the mannequin pipe was placed such that the plastic tubing protruded approximately 1 to 2 mm below the mannequin pipe, but did not touch the diaper core. Correct positioning of the plastic tube insured flow of saline solution to dispense onto the center of the diaper core and not divert to one side (leg area) of diaper. Since dosing was preformed relatively quickly, the clamp on the tubing (extending from burette or funnel) was released to start the flow of about 100 ml of saline solution into the diaper core via plastic tubing disposed within the mannequin pipe.

After the fluid reservoir was emptied, the time was set for 20 minutes. Because a dyed saline solution was used, it was easy to see where the fluid entered and dissipated into the diaper. The contour representing the core area that has been soaked with the synthetic urine was outlined and labeled on the front and back areas of the back sheet. This procedure was repeated a number of times until the 4th (100 ml each) insult had been administered.

The diaper was removed from the mannequin 700 and dried at least 24 hrs in an oven calibrated to 95° C. The top sheet was placed faced down on the oven rack, which is believed to prevent the poly and back sheet from melting in the oven. Optionally, the standing leg gathers could be removed to allow the diaper too lay flat.

The diapers then were removed from the oven and cooled for approximately ½ hr. Excess surrounds and other materials were trimmed from the absorbent garment, leaving just the core, which subsequently was weighed. Starting with $1^{st}$ insult, each area was cut along the marked contour lines representing each 100 ml insult volume. The remaining areas for insults 2, 3, and 4 also were cut. Each stained area was weighed and the weight recorded as the oven dried (o.d.) weight.

The percent utilization of the core for the $1^{st}$ 100 ml insult (MS100) was calculated in accordance with equation (12) below.

$$\% \text{ Utilization (100 ml)} \atop (MS100) = \frac{o.d. \text{ wt. of area of } 1^{st} \text{ 100 ml insult}}{o.d. \text{ wt. of total core}} \times 100 \quad (12)$$

The percent utilization of the core for the $2^{nd}$, $3^{rd}$, and $4^{th}$ 100 ml insults were calculated as follows:

$$\%Util(200 \text{ ml}) = \frac{o.d.wt.of area of 2nd 100ml insult}{o.d.wt.of total core} \times 100\% + \%Util(100 \text{ ml}) \quad (13)$$

The $3^{rd}$ and $4^{th}$ insult volumes were calculated in increasing order, each time adding the previous % Utilizations.

Leakage, Total Capacity, and Surrounds Efficiency

The purpose of this test was to determine when and the mode at which a diaper will leak while determining the effectiveness of the surrounds to contain fluid. The surrounds efficiency measures the degree of integration between the core, the leg gathers, and the top sheet in preventing leakage.

The following equipment and reagents are used in this test.
1) 500 ml burette with stopcock
2) plastic hose—attached to the end of the burette
3) stand and clamps—to hold and stabilize burette
4) sodium chloride crystals
5) blue food coloring dye
6) half baby mannequin with pipe inside (FIG. 7)
7) tray
8) de-ionized water
9) stop watch
10) 25 ml Graduated Cylinder or Larger Beaker Two (2) diapers were chosen that were a representation of the mean weight of the particular brand of diaper. Each diaper was labeled with it's dry weight, measured in accordance with the mean weight test method described above, and any other relevant information. A 0.9 wt % Saline solution without Triton-X was prepared as follows. Approximately 45 (g) of sodium chloride crystals were weighed in a dry weighing dish, and then added together with de-ionized water to a clean dry 5000 ml flask stopping at the 5000 ml mark. The concentration of the solution was measured with a refractometer to insure 0.9% concentration. About 10 drops of blue food coloring were added to add color to solution for easy viewing.

The burette was calibrated, making sure that the stand holding the burette was weighted for stability and the burette was vertical with measurements in front for easy reading. The burette was calibrated by first insuring that the stopcock was closed, and then filling it with the 0.9% saline solution. A 25 ml graduated cylinder or beaker was placed under the tube that was extending from the burette's end, and the stopcock opened to obtain a rate of approximately 1 drop/second flowing into beaker. Instead of closing the stopcock, a clamp was placed on the plastic hose to stop the flow of saline solution. When the fluid reached a recordable line, the stopwatch was started to time the flow rate for 30 seconds. After the 30 seconds, the plastic hose was clamped and the measured fluid recorded. The flow rate was determined by dividing the total amount of fluid obtained by the 30 seconds. The stopcock then was adjusted if necessary and the above procedure repeated until a target rate flowing at 5 mls/30 sec was reached. After calibrating the burette, the tube was clamped, and the burette refilled with saline solution.

The following test procedure was carried out to determine the amount of fluid dispensed up to and until the diaper leaked (ml to leakage). A diaper was opened and placed onto a mannequin using the diaper closure system (hook and loop) or tape in the same manner as that described above, with reference to FIG. 7. A suitable fit for the diaper will have the standing leg gathers 40 standing up (FIG. 1), the leg gathers 30 positioned outward (opposite diaper core), and the diaper core centered and placed close to the mannequin and around the crotch. To avoid diaper slippage, the diaper was taped to the waist area 730 near the top of the mannequin using masking tape.

Plastic tubing extending from the burette (not shown) into the top hole 720 of the mannequin pipe was placed such that the plastic tubing protruded approximately 1 to 2 mm below the mannequin pipe, but did not touch the diaper core. Correct positioning of the plastic tube insured flow of saline solution to dispense onto the center of the diaper core and not diverted to one side (leg area) of diaper. Since dosing was preformed relatively quickly, the clamp on the tubing (extending from burette or funnel) was released to start the flow of saline solution into the diaper core via plastic tubing disposed within the mannequin pipe.

The diaper and core were observed during the procedure and, when the first sign of leg leakage occurred, the tubing was re-clamped immediately and the total number of ml of synthetic urine used to cause the diaper to leak was recorded. This represented the total amount of ml of solution required for urine only leakage.

The diaper then was removed from the mannequin and the masking tape removed from the waist area. The Diaper Total Capacity test described above then was conducted on the same diaper to determine its total capacity. Immediate testing was not warranted because the diapers could be stored for a later date.

The Diaper Total Capacity and Surrounds Efficiency of each diaper then were calculated using the following equations:

$$\text{Total Capacity=Wet Diaper Weight–Dry Diaper Weight} \quad (10)$$

$$\text{Surrounds Efficiency} = \frac{\text{ml to leak} \times 1.009 \text{ g/ml}}{\text{Total Capacity g}} \quad (14)$$

Actual Leakage

The purpose of this test was to determine actual use leakage of diapers from panel participants who agreed to experimentally evaluate diapers.

A number of panelists were selected to test prototype and experimental diapers, as well as commercially available diapers. The panelists were instructed to indicate on a survey card the sex, age, and weight of the infant on whom the diaper was placed. The panelists also were instructed to complete a survey card for each diaper that was returned, and to return those diapers insulted with urine only (diapers insulted with fecal matter were not returned). The completed survey card listed the type of sleeper the baby was (e.g., AD—Awake Day, SD—Sleeping Day, or SN—Sleeping Night), whether or not the diaper leaked, and the type of leakage: (i) urine only leakage; and/or (ii) overall leakage. Twelve diapers were returned per box. The percentage of urine only leakage and overall leakage then were determined based on the survey cards returned per panelist, and the total number of diapers sampled per panelist.

The boxes so returned were opened carefully, and the information catalogued on each of the completed survey cards. The diapers then were weighed, and their weight recorded. The leakage data then can be correlated with each respective experimental or commercially available diaper, and relationships between leakage and physical properties of the respective absorbent garments can be established.

Any or all of the foregoing tests can be carried out on a number of absorbent garments. A correlation can be made between the various physical properties tested and leakage, and those physical properties that are found to have a substantially direct correlation (e.g., a correlation coefficient "r" upon linear regression analysis of the data of greater than about 0.45) with leakage can be used to design an improved leakage performance absorbent garment. Any number of the substantially directly correlated physical characteristics then can be statistically analyzed to determine the overall effect on overall leakage. For example, if 5 physical properties are found to have a direct correlation with leakage, three of the five can be statistically analyzed and regressed together with leakage to generate a 3-variable performance index that can serve as a predictor for leakage. That is, those absorbent garments having a performance index above or below a given number will leak more or less frequently. The same holds true for a 4-variable or more preferably, a five-variable performance index.

The regression equation developed based on, for example, three diaper variables can be used to predict the leakage for each sampled diaper. The predicted values then can be plotted against actual values to see how accurately the 3, 4, or 5 variable performance index regression equation can predict leakage. Accurate predictors of leakage are those that provide a correlation coefficient "r" upon linear regression analysis of the data of greater than about 0.85, and more preferably greater than about 0.9.

The present inventor has found that, based on carrying out the examples described in more detail below, and using the testing procedures outlined above, there are three, and even more preferably five physical properties that are directly related to leakage. Improving any one of these physical properties is believed to improve leakage (e.g., absorbent garment will leak less). These variables are surrounds efficiency (Se), center pad absorptive capacity under load (pad AUL), percent utilization (MS100), total capacity (Tc), and Strikethrough (Strike).

Based on the results obtained, the invention encompasses a method of designing an absorbent article to have reduced urine only leakage comprising modifying one or more absorbent article variables by carrying out one or more procedures selected from: (i) increasing the front pad absorbent capacity under load (AUL) to a value of about 23 grams of fluid/gram of material or more; (ii) increasing the percent utilization of the absorbent core (MS100) to a value of about 43% or more; (iii) increasing the surrounds efficiency (Se) to a value of about 90% or more; (iv) decreasing the third void strikethrough (St) to a value of less than about 30 seconds; and (v) increasing the total capacity of the absorbent article (Tc) to a value of less than about 495 grams, and more than about 465 grams. It is preferred in the present invention that more than one of the above variables is modified as described.

Those skilled in the art are capable of modifying various components of the absorbent article to modify any or all of the above described variables. For example, use of a superabsorbent polymer having a greater absorbent capacity under load (e.g., higher AUL) can increase the total capacity, the front pad absorbent capacity under load, and strikethrough. Use of an acquisition layer having improved acquisition properties can reduce the $3^{rd}$ void strikethrough, as well as enhance the total capacity by enabling more liquid to reach the absorbent core. Improving the top sheet's, acquisition layer's and fibrous material in the core's ability to vertically and longitudinally wick fluid also can improve the front pad AUL and total capacity. Using stronger or more elastic components in the leg gathers of the diapers, as well as using larger leg gathers, can improve the surrounds efficiency. Other techniques suitable for modifying any of the aforementioned absorbent article variables can be used in the invention, and will be readily apparent to those skilled in the art, upon review of the description and guidelines provided herein.

The invention also includes a method of designing an absorbent article to have reduced overall leakage comprising modifying one or more absorbent article variables by carrying out one or more procedures selected from: (i) increasing the front pad absorbency under load (AUL) to a value of about 23 grams of fluid/gram of material or more; (ii) increasing the percent utilization of the absorbent core (MS100) to a value of about 43% or more; (iii) increasing the surrounds efficiency (Se) to a value of about 89% or more; (iv) decreasing the third void strikethrough (St) to a value of less than about 38 seconds; and (v) increasing the total capacity of the absorbent article (Tc) to a value of about 495 grams or more. It is preferred in the present invention that more than one of the above variables is modified as described. These absorbent article variables can be modified in the same manner as described above.

The invention also includes a method of designing an absorbent article having reduced leakage that includes measuring a plurality of variables on a plurality of different absorbent articles. The method also includes determining the percentage of the plurality of absorbent articles that leak (urine only or overall leakage percentage) through actual use tests, and then determining which of the plurality of variables for the plurality of absorbent articles provides a substantially direct correlation with the leakage percentage (urine only or overall) to produce at least one leakage variable that directly correlates with leakage percentage. The method then includes adjusting at least one of the at least one leakage variable to reduce the leakage percentage of the absorbent article.

The method of the invention can be illustrated more fully by the following non-limiting example. Those skilled in the art will appreciate the various modifications that can be made to the invention, using the guidelines and teaching herein.

EXAMPLES

A number of ten different brands of commercially available Stage 4 diapers were obtained, and subjected to the test methods described in the test methods section above. The absorbent articles also were subjected to actual use tests to determine the percentage of urine only leakage and overall leakage. The results obtained are tabulated below in Tables 1 and 2.

TABLE 1

| Sample | % Leak Urine only | % Leak Overall | ml to Leakage | Se | MS300 |
|---|---|---|---|---|---|
| A | 5.79 | 7.7 | 353 | 0.71 | 0.6 |
| B | 5.23 | 7.1 | 429 | 0.86 | 0.55 |
| C | 14.44 | 22.1 | 273 | 0.44 | 0.42 |
| D | 3.53 | 5.63 | 498 | 0.89 | 0.52 |
| E | 4.3 | 6.8 | 484 | 0.86 | 0.52 |
| F | 4.34 | 4.5 | 370 | 0.78 | 0.56 |
| G | 2.89 | 4.53 | 475 | 0.8 | 0.54 |
| H | 3.24 | 6.93 | 395 | 0.82 | 0.54 |
| I | 3.11 | 5.73 | 403 | 0.84 | 0.58 |
| J | 4.09 | 6.65 | 400 | 0.93 | 0.53 |

Se is Surrounds efficiency;
MS300 is percent utilization for 300 ml.

TABLE 2

| Sample | % Leak Urine only | % Leak Overall | MS100 | pad AUL | Tc | St |
|---|---|---|---|---|---|---|
| A | 5.79 | 7.7 | 0.47 | 20.3 | 499 | 48 |
| B | 5.23 | 7.1 | 0.4 | 21.7 | 457 | 46 |
| C | 14.44 | 22.1 | 0.31 | 17.4 | 618 | 306 |
| D | 3.53 | 5.63 | 0.39 | 27.6 | 568 | 50 |
| E | 4.3 | 6.8 | 0.38 | 23.7 | 565 | 59 |
| F | 4.34 | 4.5 | 0.44 | 19.2 | 479 | 89 |
| G | 2.89 | 4.53 | 0.4 | 27.7 | 577 | 88 |
| H | 3.24 | 6.93 | 0.4 | 20.9 | 489 | 56 |
| I | 3.11 | 5.73 | 0.39 | 18.3 | 452 | 52 |
| J | 4.09 | 6.65 | 0.49 | 18.7 | 437 | 57 |

Tc is total capacity;
MS100 is percent utilization for 100 ml;
St is the third void strikethrough in seconds.

The above variables all were plotted against urine only leakage and overall leakage to determine which variables had a substantially direct correlation to the leakage. The variables found to have a substantially direct correlation to urine only and overall leakage were the surrounds efficiency (Se), pad AUL (AUL), percent utilization for 100 ml (MS100), total capacity (Tc), and third void strikethrough (St). The various graphs illustrating the respective correlations are shown in FIGS. 8-17.

Figure 8:
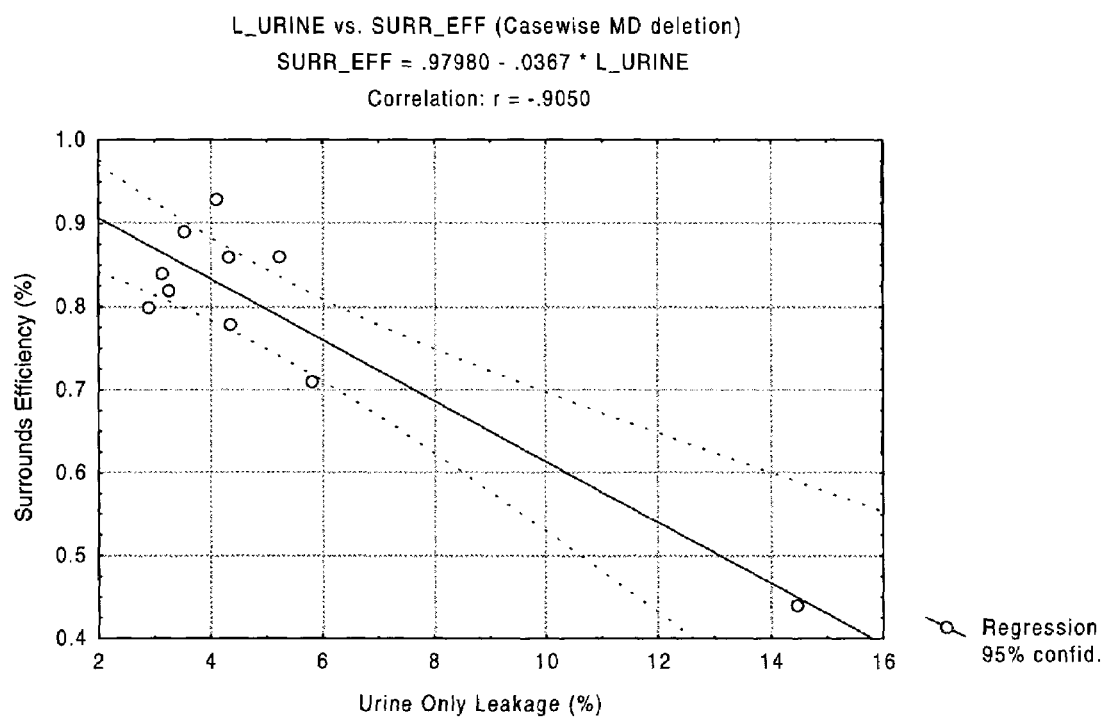
FIG. 8 is a graph showing the relationship between surrounds efficiency and urine only leakage.
Figure 9:
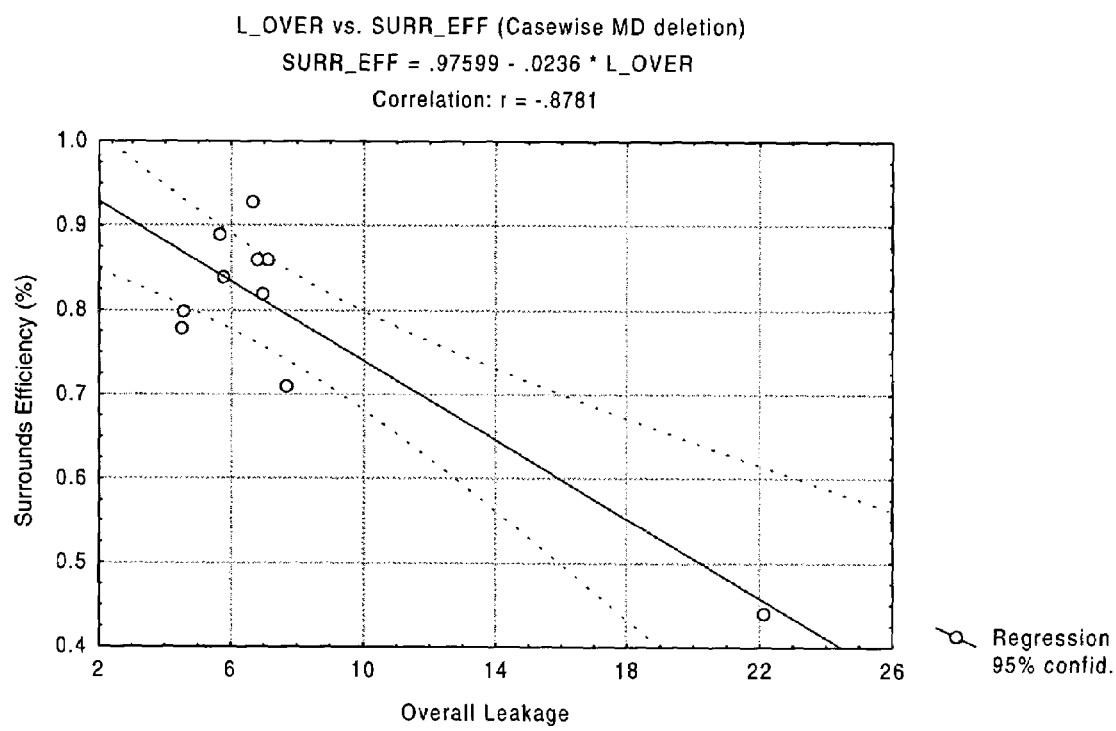
FIG. 9 is a graph showing the relationship between surrounds efficiency and overall leakage.

FIGS. 8 and 9 illustrate the relationship between surrounds efficiency and urine only leakage (FIG. 8), and overall leakage (FIG. 9). The regression equations reveal the following correlations set forth in equations 15 and 16:

$$Se=0.97980-0.0367(Lu) \quad (15)$$

$$Se=0.97599-0.0236(Lo) \quad (16)$$

where Lu is urine only leakage, and Lo is overall leakage.

Figure 10:
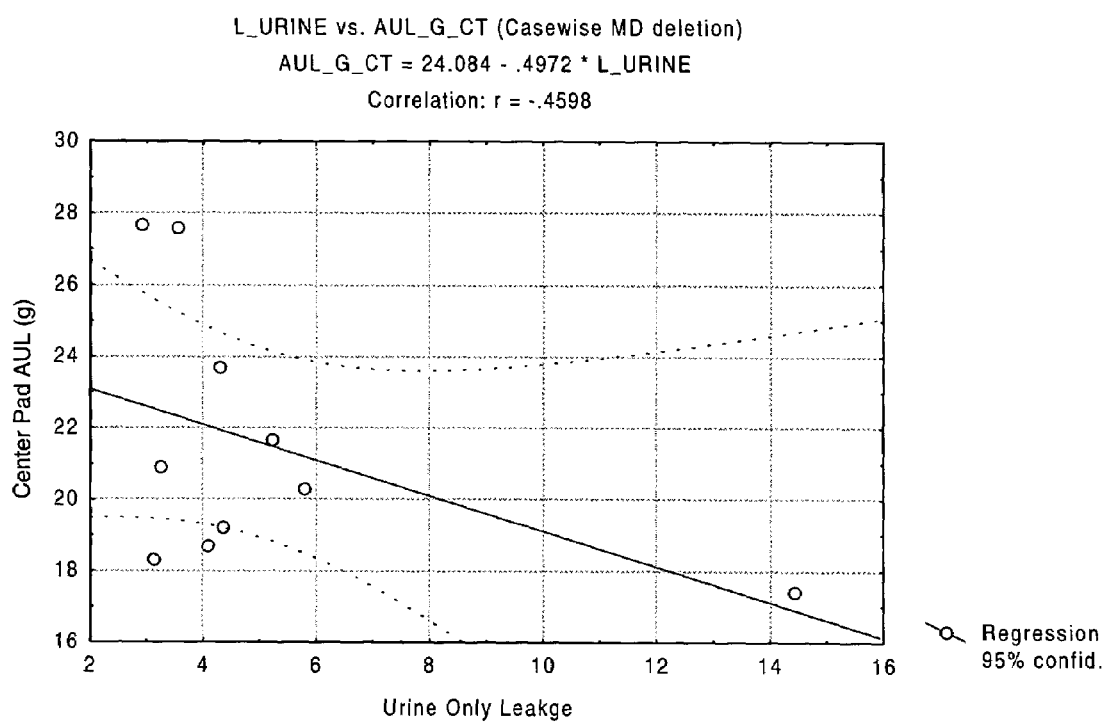
FIG. 10 is a graph showing the relationship between front pad AUL and urine only leakage.
Figure 11:
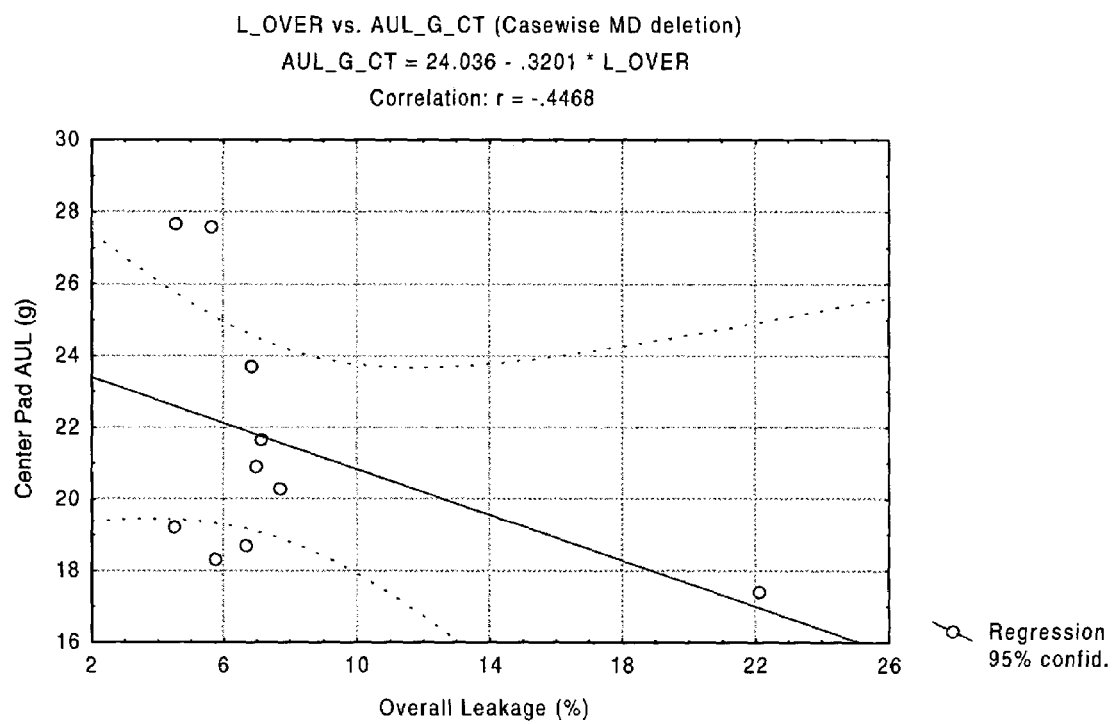
FIG. 11 is a graph showing the relationship between front pad AUL and overall leakage.

FIGS. 10 and 11 illustrate the relationship between front pad AUL and urine only leakage (FIG. 10), and overall leakage (FIG. 11). The regression equations reveal the following correlations set forth in equations 17 and 18:

$$AUL=24.084-0.4972(Lu) \quad (17)$$

$$AUL=24.036-0.321(Lo) \quad (18)$$

Figure 12:
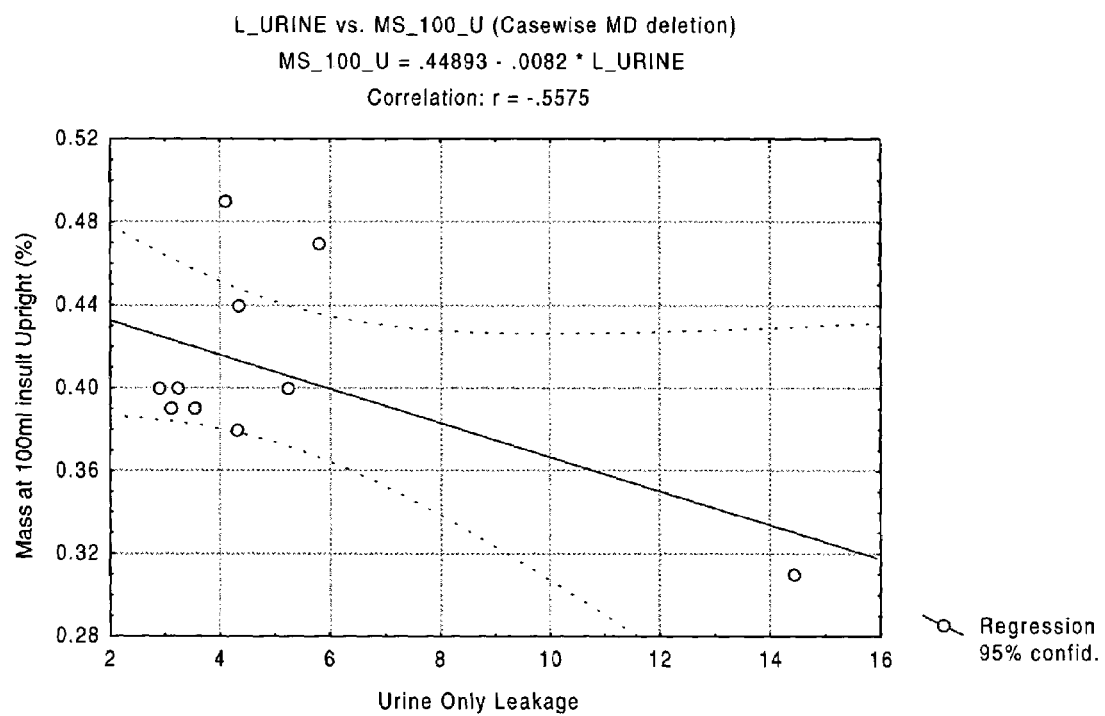
FIG. 12 is a graph showing the relationship between percent utilization and urine only leakage.
Figure 13:
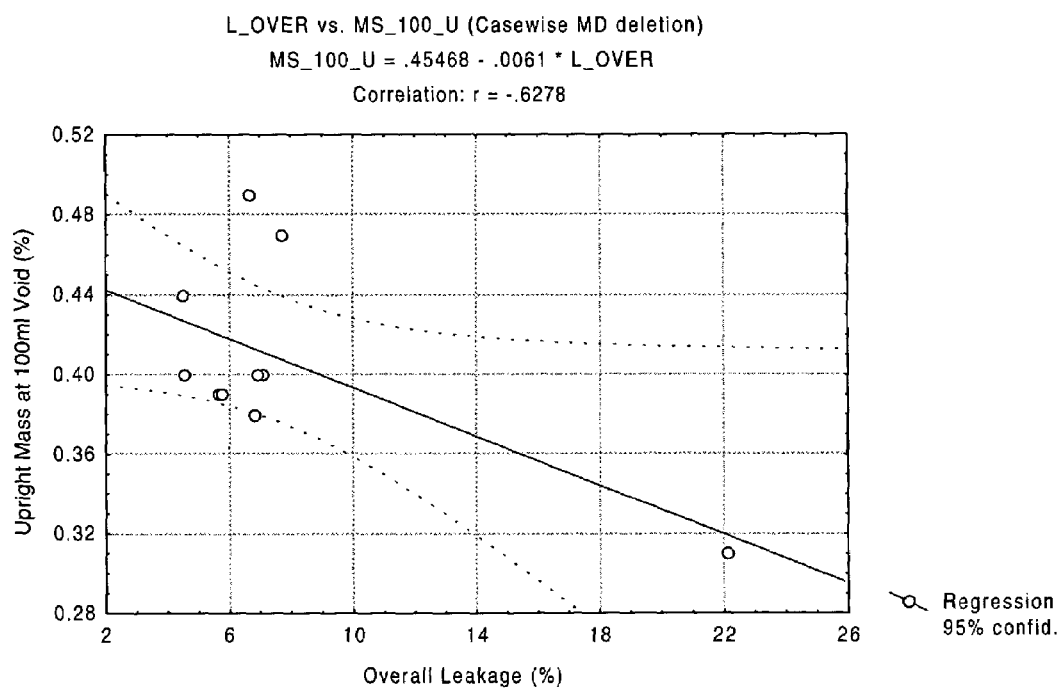
FIG. 13 is a graph showing the relationship between percent utilization and overall leakage.

FIGS. 12 and 13 illustrate the relationship between percent utilization with 100 ml of synthetic saline and urine only leakage (FIG. 12), and overall leakage (FIG. 13). The regression equations reveal the following correlations set forth in equations 19 and 20:

$$MS100=0.44893-0.0082(Lu) \quad (19)$$

$$MS100=0.45468-0.0061(Lo) \quad (20)$$

Figure 14:
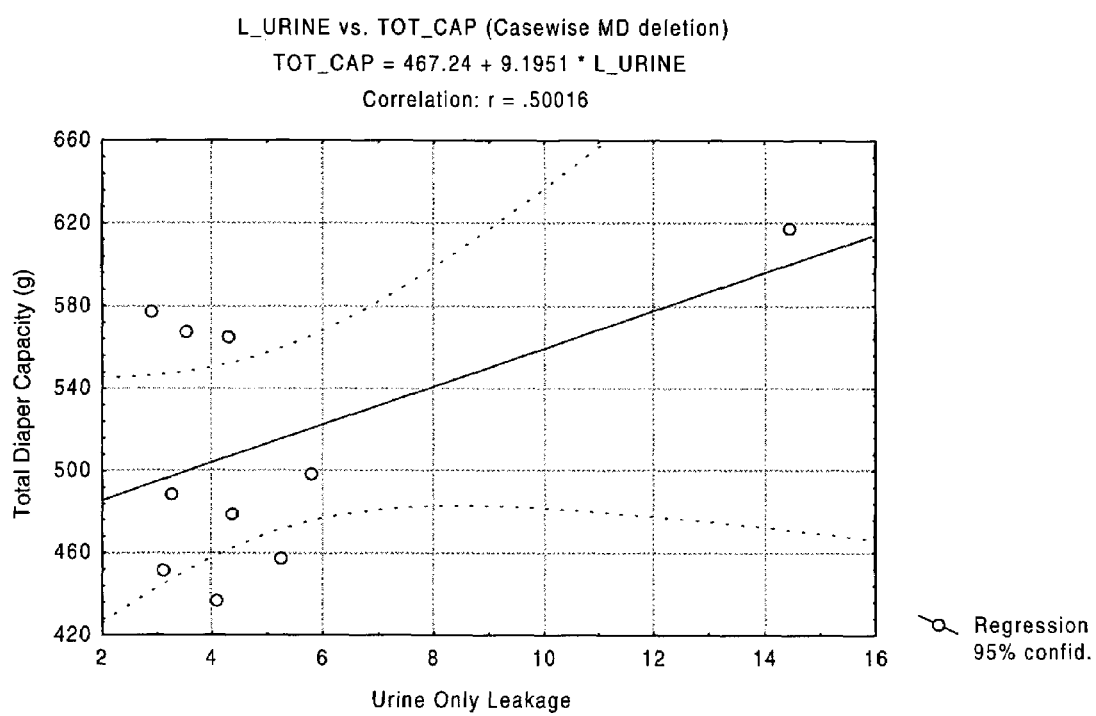
FIG. 14 is a graph showing the relationship between total capacity and urine only leakage.
Figure 15:
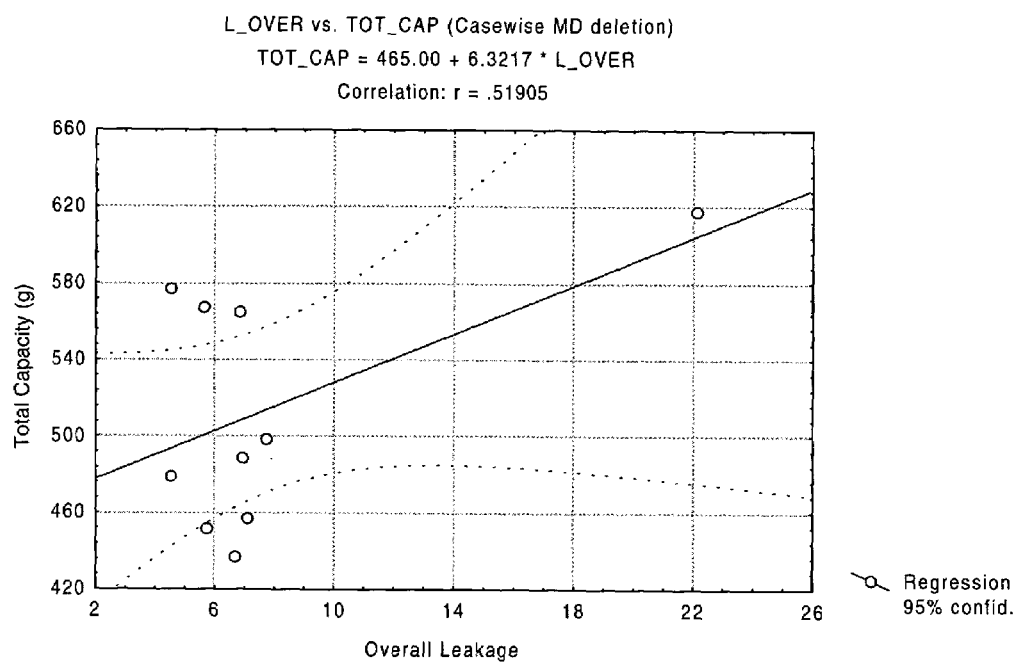
FIG. 15 is a graph showing the relationship between total capacity and overall leakage.

FIGS. 14 and 15 illustrate the relationship between total capacity (Tc) and urine only leakage (FIG. 14), and overall leakage (FIG. 15). The regression equations reveal the following correlations set forth in equations 21 and 22:

$$Tc=467.24+9.1951(Lu) \quad (21)$$

$$Tc=465.0+6.3217(Lo) \quad (22)$$

Figure 16:
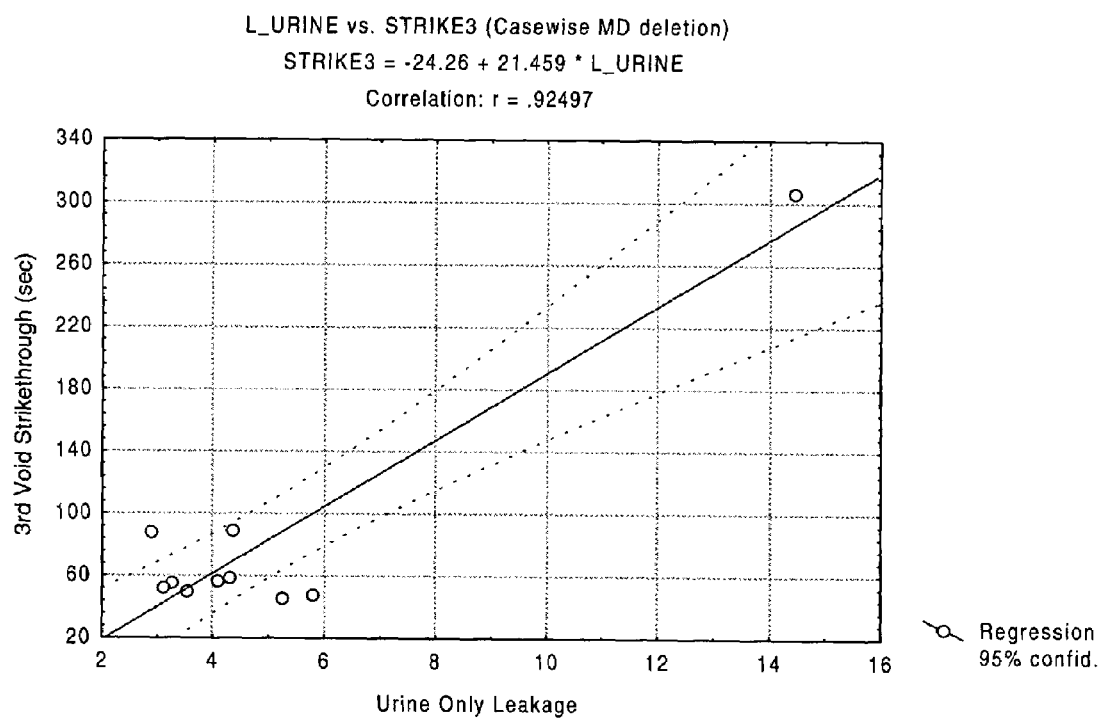
FIG. 16 is a graph showing the relationship between third void strikethrough and urine only leakage.
Figure 17:
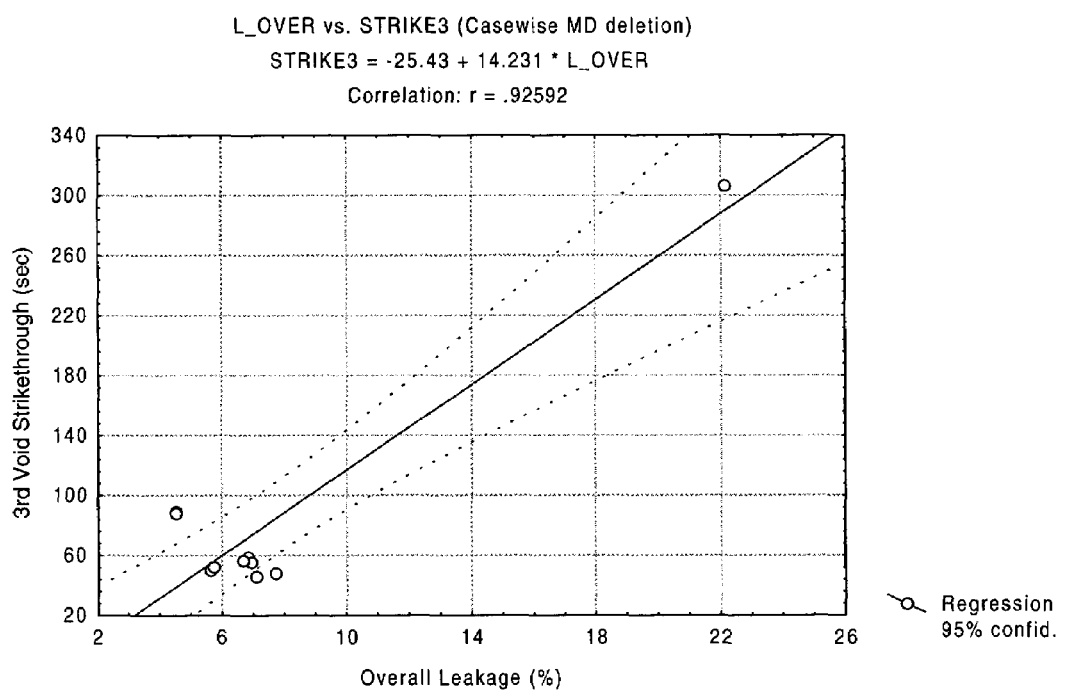
FIG. 17 is a graph showing the relationship between third void strikethrough and overall leakage.

FIGS. 16 and 17 illustrate the relationship between third void strikethrough (St) and urine only leakage (FIG. 16), and overall leakage (FIG. 17). The regression equations reveal the following correlations set forth in equations 23 and 24:

$$St=-24.26+21.459(Lu) \quad (23)$$

$$St=-25.43+14.231(Lo) \quad (24)$$

Ideally, one could drive leakage, both urine only and overall leakage, to zero, but absorbent articles having zero percent leakage are not practical. The five variables mentioned above sometimes interact with one another in the sense that raising one value may have the effect of lowering another. For example, enhancing the total capacity by using more SAP in the absorbent core may make the absorbent article bulky and adversely affect the surrounds efficiency. Increasing the pad AUL also may have an adverse affect on MS100, or percent utilization of the core. It therefore is desirable to assess the overall effect various combinations of these variables have on urine only and overall leakage.

Figure 18:
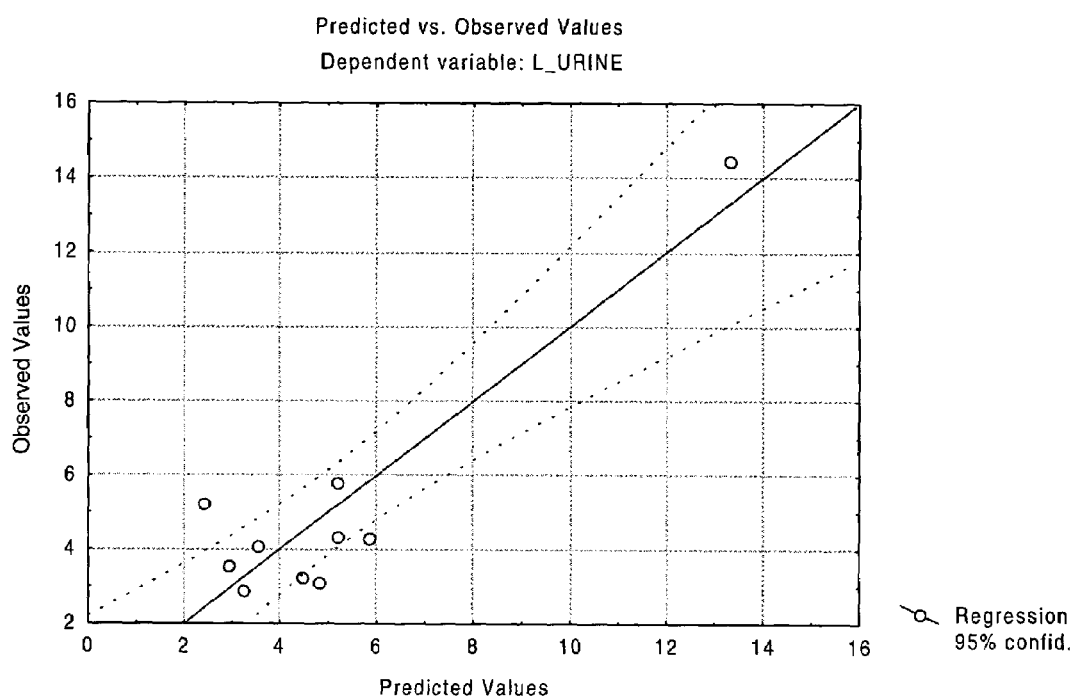
FIG. 18 is a graph showing the relationship between actual urine only leakage, and urine only leakage predicted by three variables.

FIGS. 18-21 are graphs showing the relationship between predicted leakage values, and actual leakage values using three of the above variables, and using all five of the above variables. FIG. 18 shows the linear relationship between predicted and actual urine only leakage values using three variables. The value of r in FIG. 18 was 0.91, $r^2$ being 0.83, thereby indicating a nearly linear relationship. The three variable urine only leakage equation developed by the regression analysis depicted in FIG. 18 is represented in equation (25) below.

$$Lu=-0.551-2.94(MS100)-0.772(AUL)+0.046(Tc) \quad (25)$$

Equation 25 then was used to determine the three variable urine only leakage Performance Index. The three variable urine only leakage Performance Index was determined by using the minimum urine only leakage value (2.89 for absorbent article G) as Lu, which yields the following equation (26):

$$3.441=0.046(Tc)-2.94(MS100)-0.772(AUL) \quad (26)$$

If Lu were zero, then the left hand side of equation (26) would be 0.551. The Performance Index therefore was set to be less than 3.441, preferably less than 3.0 for an improved absorbent article, whereby the minimum value for the Performance Index preferably is 0.6. Accordingly, the three variable urine only leakage Performance Index was developed as the following equation (1):

$$PI_{3UL}=0.046(Tc)-2.94(MS100)-0.772(AUL) \quad (1)$$

Figure 19:
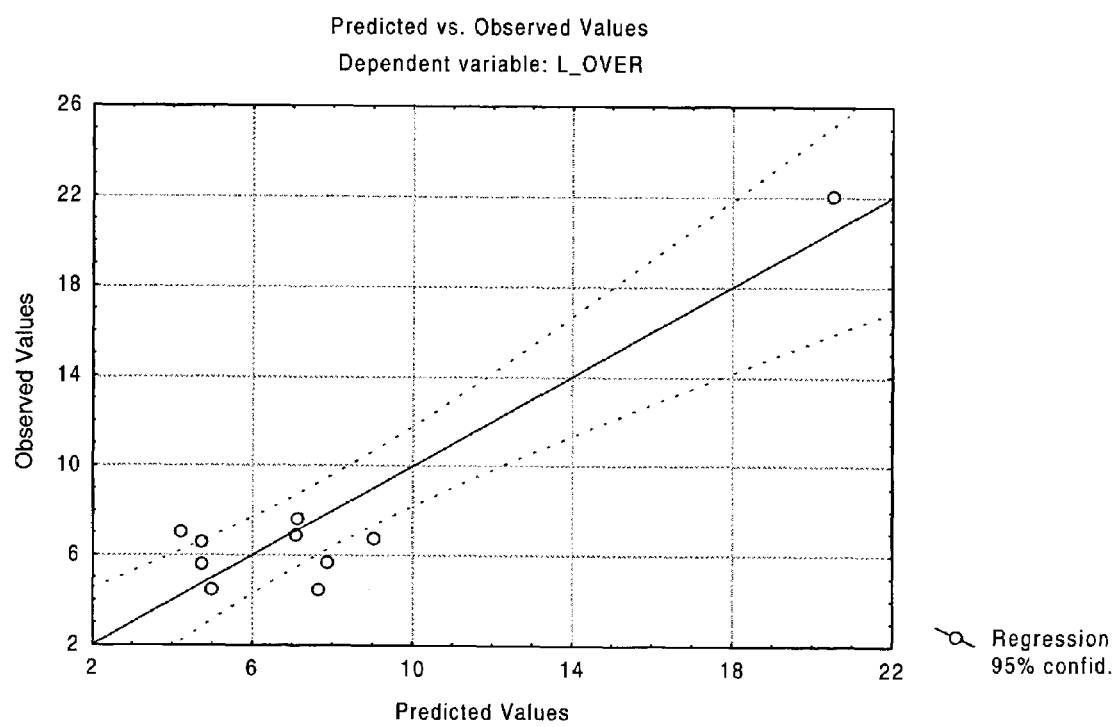
FIG. 19 is a graph showing the relationship between actual urine only leakage, and urine only leakage predicted by five variables.

FIG. 19 shows the linear relationship between predicted and actual overall leakage values using three variables. The value of r in FIG. 19 was 0.92, $r^2$ being 0.85, thereby indicating nearly linear relationship. The three variable overall leakage equation developed by the regression analysis depicted in FIG. 19 is represented in equation (27) below.

$$Lo=7.05-17.544(MS100)-1.107(AUL)+0.062(Tc) \quad (27)$$

Equation 27 then was used to determine the three variable overall leakage Performance Index. The three variable overall leakage Performance Index was determined by using the minimum overall leakage value (4.5 for absorbent article F) as Lo, which yields the following equation (28):

$$-2.55 = 0.062(Tc) - 17.54(MS100) - 1.107(AUL) - \qquad (28)$$

Figure 20:
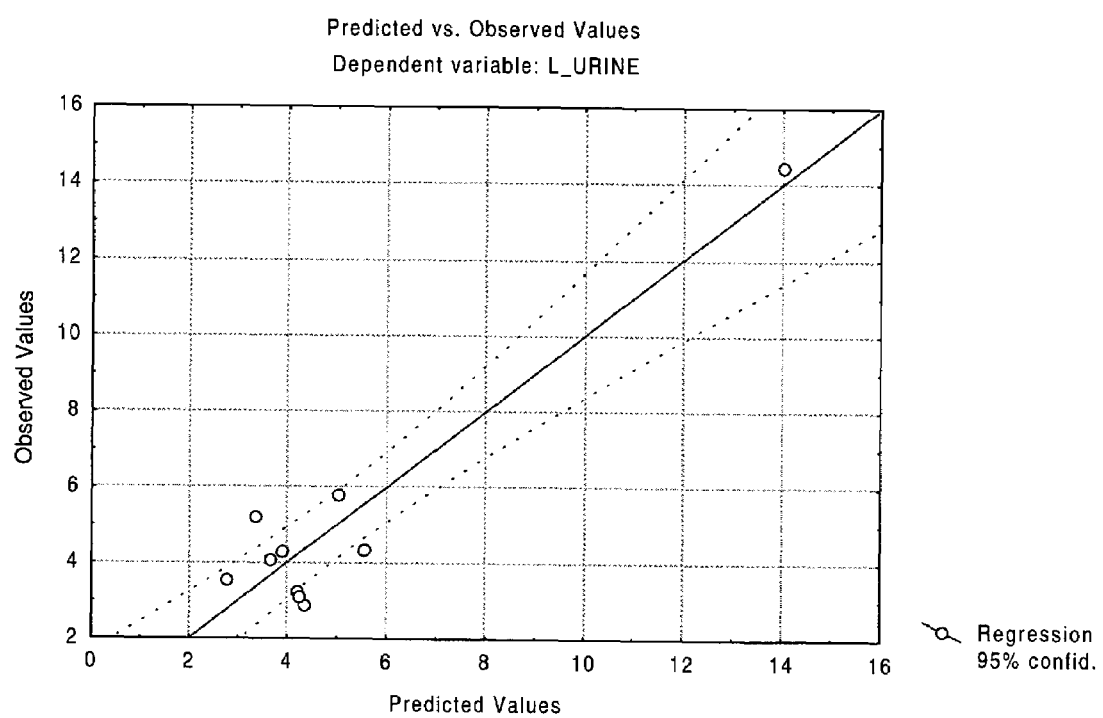
FIG. 20 is a graph showing the relationship between actual overall leakage, and overall leakage predicted by three variables.

If Lo were zero, then the left hand side of equation (28) would be −7.05. The Performance Index therefore was set to be less than negative 2.55, preferably less than negative 2.65 for an improved absorbent article, whereby the minimum value for the Performance Index preferably is negative 7.0. Accordingly, the three variable overall leakage Performance Index was developed as the following equation (3):

FIG. 20 shows the linear relationship between predicted and actual urine only leakage values using five variables. The value of r in FIG. 20 was 0.95, $r^2$ being 0.895, thereby indicating a nearly linear relationship. The five variable urine only leakage equation developed by the regression analysis depicted in FIG. 20 is represented in equation (29) below.

$$Lu = 9.34 - 7.09(Se) + 1.107(MS100) - 0.183(AUL) + 0.006(Tc) + 0.023(St) \qquad (29)$$

Equation 29 then was used to determine the five variable urine only leakage Performance Index. The five variable urine only leakage Performance Index was determined by using the minimum overall leakage value (2.89 for absorbent article G) as Lu, which yields the following equation (30):

$$-6.45 = -7.09(Se) + 1.107(MS100) - 0.183(AUL) + 0.006(Tc) + 0.023(St) \qquad (30)$$

If Lu were zero, then the left hand side of equation (30) would be −9.34. The Performance Index therefore was set to be less than negative 6.45, preferably less than negative 6.4 for an improved absorbent article, whereby the minimum value for the Performance Index preferably is negative 9.3. Accordingly, the five variable urine only leakage Performance Index was developed as the following equation (2):

$$PI_{SUL} = 0.006(Tc) - 7.094(Se) + 1.108(MS100) - 0.18(AUL) + 0.023(St) \qquad (2)$$

Figure 21:
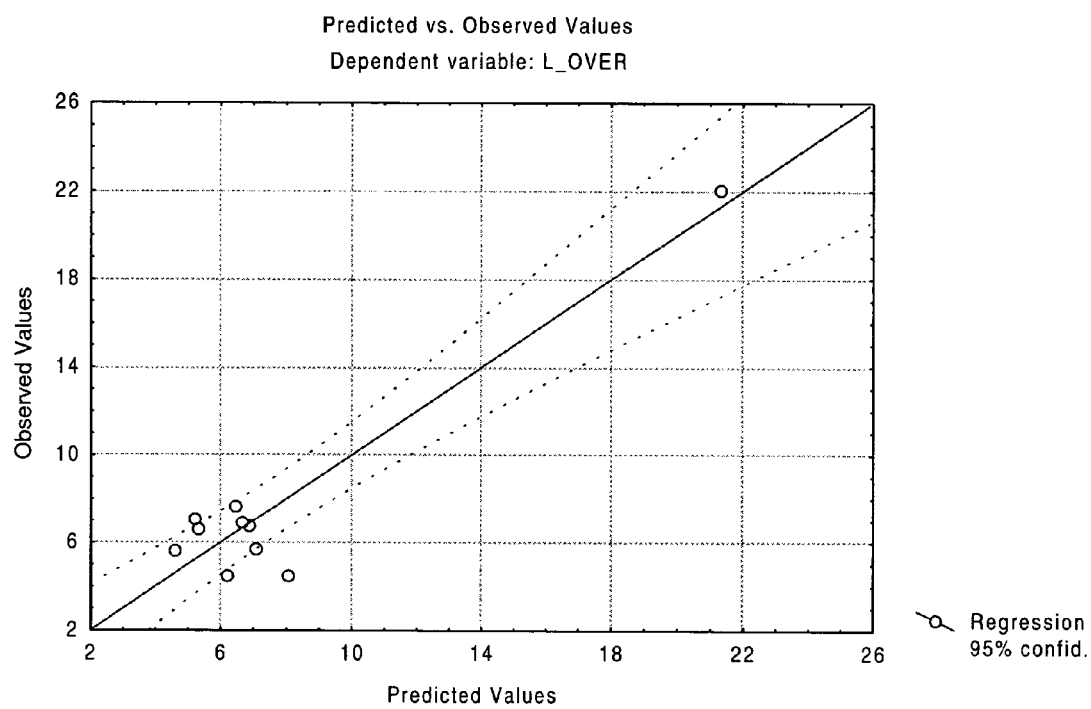
FIG. 21 is a graph showing the relationship between actual overall leakage, and overall leakage predicted by five variables.

FIG. 21 shows the linear relationship between predicted and actual overall leakage values using five variables. The value of r in FIG. 21 was 0.94, $r^2$ being 0.89, thereby indicating a nearly linear relationship. The five variable overall leakage equation developed by the regression analysis depicted in FIG. 21 is represented in equation (31) below.

$$Lo = 13.3 - 3.75(Se) - 11.35(MS100) - 0.465(AUL) + 0.018(Tc) + 0.033(St) \qquad (31)$$

Equation 31 then was used to determine the five variable overall leakage Performance Index. The five variable overall leakage Performance Index was determined by using the minimum overall leakage value (4.5 for absorbent article F) as Lo, which yields the following equation (32):

$$-8.8 = -3.75(Se) - 11.35(MS100) - 0.465(AUL) + 0.018(Tc) + 0.033(St) \qquad (32)$$

If Lo were zero, then the left hand side of equation (32) would be −13.3. The Performance Index therefore was set to be less than negative 8.8, preferably less than negative 9.3 for an improved absorbent article, whereby the minimum value for the Performance Index preferably is negative 13.0. Accordingly, the five variable overall leakage Performance Index was developed as the following equation (4):

$$PI_{SOL} = 0.018(Tc) - 3.75(Se) - 11.35(MS100) - 0.465(AUL) + 0.033(St) \qquad (4)$$

The above linear relationships indicate that decreasing the amount of leakage can be achieved by any one or more of the following: (i) increasing the surrounds efficiency; (ii) increasing the center pad absorptive capacity; (iii) increasing the utilization of the core; (iv) increasing the total capacity of the garment; and (v) decreasing the strikethrough time. The equations also reveal that an absorbent garment can be designed to have minimal urine only leakage by formulating the garment to have any one or more of the following physical properties: (i) a surrounds efficiency (Se)≧about 90%; (ii) a front pad AUL≧about 23 grams; (iii) a percent utilization (MS100) of ≧about 43%; (iv) a total capacity (Tc)≦about 495 grams; and (v) a third void Strikethrough time (St)≦about 30 seconds. It is preferred that the absorbent garment have at least three of the aforementioned physical properties, more preferably at least four, and most preferably at least five.

The equations also reveal that an absorbent garment can be designed to have minimal overall leakage by formulating the garment to have any one or more of the following physical properties: (i) a surrounds efficiency (Se)≧about 89%; (ii) a front pad AUL≧about 23 grams; (iii) a percent utilization (MS100) of ≧about 43%; (iv) a total capacity (Tc)≦about 495 grams; and (v) a third void Strikethrough time (St) ≦about 38 seconds. It is preferred that the absorbent garment have at least three of the aforementioned physical properties, more preferably at least four, and most preferably at least five.

It is preferred that the surrounds efficiency of the absorbent garment of the present invention be greater than about 92%, more preferably, greater than about 93%, even more preferably greater than about 93.5%, and most preferably greater than about 94%. The surrounds efficiency can be improved in any number of ways. For example, the number and/or elastic strength of the leg gathers, the height of the standing leg gathers can be enhanced, the phobicity of the material used can be altered, and the absorbency of the core increased, etc. This will serve to improve the "leg gasketing" effect. It is preferred that the absorbent garment of the invention include standing leg gathers, and that the standing leg gathers satisfy the leg gasketing characteristics (leg gasketing index, etc.) set forth in copending U.S. patent application Ser. No. 10/046, 553, entitled: "Leg Gasketing Index for Absorbent Undergarments," filed on Jan. 16, 2002. Another mechanism by which the surrounds efficiency can be improved is to use multiple standing leg gathers (e.g., "dual cuff") arrangement, such as that described in U.S. Pat. Nos. 4,695,278, and 4,795,454, the disclosures of which are incorporated by reference herein in their entirety. Using the guidelines provided herein, those skilled in the art will recognize other means for enhancing the surrounds efficiency of the absorbent garment of the invention.

It is preferred that the pad AUL of the absorbent garment of the present invention be greater than about 23.5, more preferably, greater than about 23.75, even more preferably greater than about 24, and most preferably greater than about 24.1 grams of 0.9 wt % saline solution absorbed per gram of pad material. The pad AUL can be improved in any number of ways. For example, the type and/or amount of superabsorbent polymer (SAP) can be modified to provide a better absorbent SAP, the type of fiber component used in the pad can be modified to provide a more absorbent fiber, or a fiber having greater wicking properties, additional wicking layers or transfer layers may be employed, etc. Using the guidelines provided herein, those skilled in the art will recognize other means for enhancing the pad AUL of the absorbent garment of the invention.

It is preferred that the percent utilization (MS100) of the absorbent garment of the present invention be greater than about 43%, more preferably, greater than about 43.5%, even more preferably greater than about 44%, and most preferably greater than about 44.5%. The percent utilization can be improved in any number of ways. For example, the type and/or amount of superabsorbent polymer (SAP) can be modified to provide a better absorbent SAP, the type of fiber component used in the pad can be modified to provide a more absorbent fiber, or a fiber having greater wicking properties, and the type of acquisition layer material can be modified to provide a better horizontal and vertical wicking material. Using the guidelines provided herein, those skilled in the art will recognize other means for enhancing the percent utilization of the absorbent core of the absorbent garment of the invention.

It is preferred that the total capacity (Tc) of the absorbent garment of the present invention be maintained at a value between about 465 grams and about 495 grams, more preferably, between about 465 and about 490, even more preferably between about 465 and about 485, and most preferably between about 470 and about 495. The total capacity can be maintained within the above ranges in any number of ways. For example, the type and/or amount of superabsorbent polymer (SAP) can be modified to provide a better absorbent SAP, the type of fiber component used in the pad can be modified to provide a more absorbent fiber, or a fiber having greater wicking properties, and thinner materials can be used. Using the guidelines provided herein, those skilled in the art will recognize other means for enhancing the total capacity of the absorbent garment can be maintained within the ranges preferred herein.

It is preferred that the third void strikethrough (St) of the absorbent garment of the present invention be less than about 35 seconds, more preferably, less than about 30 seconds, even more preferably less than about 28 seconds, and most preferably less than about 27 seconds. The third void strikethrough can be improved in any number of ways. For example, the type and/or amount of superabsorbent polymer (SAP) can be modified to provide a better absorbent SAP, the type of fiber component used in the pad can be modified to provide a more absorbent fiber, or a fiber having greater wicking properties, and the type of acquisition layer material can be modified to provide a better horizontal and vertical wicking material. Using the guidelines provided herein, those skilled in the art will recognize other means for enhancing the third void strikethrough of the absorbent garment of the invention.

While the invention has been described in detail with reference to particularly preferred embodiments, those skilled in the art will recognize that various modifications may be made to the invention without departing from the spirit and scope thereof.

What is claimed is:

1. An absorbent article comprising a top sheet, a back sheet, an absorbent core disposed between the top sheet and the back sheet, and in insult point, the absorbent core having a basis weight that is substantially equal to a basis weight of the insult point, whereby the absorbent article has a 3 variable urine only leakage performance index ($PI_{3UL}$) of less than about 3.0, the $PI_{3UL}$ being determined in accordance with the following equation (1):

$$PI_{3UL}=0.046(Tc)-2.94(MS100)-0.772(AUL) \quad (1)$$

where Tc is the total capacity in grams, MS100 is the percent utilization of the core upon insult with 100 ml of 0.9 wt % saline solution, and AUL is the front pad absorbency under load of the absorbent article, expressed in grams of 0.9 wt % saline solution absorbed per gram of pad material, the AUL having a value of about 23 grams of fluid/gram of material or more.

2. The absorbent article of claim 1, wherein the 3 variable urine only leakage performance index ($PI_{3UL}$) is less than about 2.9.

3. The absorbent article of claim 1, wherein the 3 variable urine only leakage performance index ($PI_{3UL}$) is less than about 2.7.

4. The absorbent article of claim 1, wherein the 3 variable urine only leakage performance index ($PI_{3UL}$) is within the range of from about 0.5 to about 2.9.

5. The absorbent article of claim 1, wherein the 3 variable urine only leakage performance index ($PI_{3UL}$) is within the range of from about 0.75 to about 2.7.

6. The absorbent article of claim 1, wherein the absorbent article is a Stage 4 diaper.

7. An absorbent article comprising a top sheet, a back sheet, an absorbent core disposed between the top sheet and the back sheet, and an insult point, the absorbent core having a basis weight that is substantially equal to a basis weight of the insult point, whereby the absorbent article has a five variable urine only leakage Performance Index ($PI_{5UL}$) of less than about negative 6.4, whereby $PI_{5UL}$ is determined in accordance with the following equation (2):

$$PI_{5UL}=0.006(Tc)-7.094(Se)+1.108(MS100)-0.18(AUL)+0.023-(St) \quad (2)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, expressed in grams of 0.9 wt % saline solution absorbed per gram of pad material, the AUL having a value of about 23 grams of fluid/gram of material or more.

8. The absorbent article of claim 7, wherein the five variable urine only leakage Performance Index ($PI_{5UL}$) is less than about negative 6.5.

9. The absorbent article of claim 7, wherein the five variable urine only leakage Performance Index ($PI_{5UL}$) is less than about negative 6.75.

10. The absorbent article of claim 7, wherein the five variable urine only leakage Performance Index ($PI_{5UL}$) is within the range of from about negative 9.3 to about negative 6.4.

11. The absorbent article of claim 7, wherein the five variable urine only leakage Performance Index ($PI_{5UL}$) is within the range of from about negative 8.75 to about negative 6.75.

12. The absorbent article of claim 7, wherein the absorbent article is a Stage 4 diaper.

13. A method of making the absorbent article of claim 7 comprising providing a top sheet, a back sheet, and an absorbent core to a garment forming station; and disposing the absorbent core at least partially between the top sheet and the back sheet at the garment forming station to form the absorbent article.

14. The method of claim 13, wherein the five variable urine only leakage Performance Index ($PI_{5UL}$) is less than about negative 6.5.

15. The method of claim 13, wherein the five variable urine only leakage Performance Index ($PI_{5UL}$) is less than about negative 6.75.

16. The method of claim 13, wherein the five variable urine only leakage Performance Index ($PI_{5UL}$) is within the range of from about negative 9.3 to about negative 6.4.

17. The method of claim 13, wherein the five variable urine only leakage Performance Index ($PIPI_{5_{UL}}$) is within the range of from about negative 8.75 to about negative 6.75.

18. The method of claim 7, wherein the absorbent article is a Stage 4 diaper.

19. An absorbent article comprising a top sheet, a back sheet, an absorbent core disposed between the top sheet and the back sheet, and an insult point, the absorbent core having a basis weight that is substantially equal to a basis weight of the insult point, whereby the absorbent article has a 3 variable overall leakage performance index ($P_{3OL}$) of less than about negative 2.65, whereby the $PI_{3OL}$ is determined in accordance with the following equation (3):

$$PI_{3OL}=0.062(Tc)-17.54(MS100)-1.107(AUL) \quad (3)$$

where Tc is the total capacity, MS100 is the percent utilization of the core upon insult with 100 ml of 0.9 wt % saline solution, and AUL is the front pad absorbency under load of the absorbent article, expressed in grams of 0.9 wt % saline solution, the AUL having a value of about 23 grams of fluid/gram of material or more.

20. The absorbent article of claim 19, wherein the 3 variable overall leakage performance index ($PI_{3OL}$) is less than about negative 2.75.

21. The absorbent article of claim 19, wherein the 3 variable overall leakage performance index ($PI_{3OL}$) is less than about negative 2.9.

22. The absorbent article of claim 19, wherein the 3 variable overall leakage performance index ($PI_{3OL}$) is within the range of from about negative 7.0 to about negative 2.65.

23. The absorbent article of claim 19, wherein the 3 variable overall leakage performance index ($PI_{3OL}$) is within the range of from about negative 6.3 to about negative 2.9.

24. The absorbent article of claim 19, wherein the absorbent article is a Stage 4 diaper.

25. An absorbent article comprising a top sheet, a back sheet, an absorbent core disposed between the top sheet and the back sheet, and an insult point, the absorbent core having a basis weight that is substantially equal to a basis weight of the insult point, whereby the absorbent article has a five variable overall leakage Performance Index ($PI_{5OL}$) of less than about negative 9.3, whereby $PI_{5OL}$ is determined in accordance with the following equation (4):

$$PI_{5OL}=0.018(Tc)-3.75(Se)-11.35(MS100)-0.465(AUL)+0.033-(St) \quad (4)$$

where Se is surrounds efficiency, St is the third void strikethrough, Tc is the total capacity, MS100 is the percent utilization of the core upon insult with 100 ml of 0.9 wt % saline solution, and AUL is the front pad absorbency under load of the absorbent article, expressed in grams of 0.9 wt % saline solution, the AUL having a value of about 23 grams of fluid/gram of material or more.

26. The absorbent article of claim 25, wherein the five variable overall leakage Performance Index ($PI_{5OL}$) is less than about negative 9.45.

27. The absorbent article of claim 25, wherein the five variable overall leakage Performance Index ($PI_{5OL}$) is less than about negative 9.75.

28. The absorbent article of claim 25, wherein the five variable overall leakage Performance Index ($PI_{5OL}$) is within the range of from about negative 13.0 to about negative 9.3.

29. The absorbent article of claim 25, wherein the five variable overall leakage Performance Index ($PI_{5OL}$) is within the range of from about negative 12.35 to about negative 9.75.

30. The absorbent article of claim 25, wherein the absorbent article is a Stage 4 diaper.

31. A method of designing an absorbent article to have reduced urine only leakage comprising modifying one or more absorbent article variables by carrying out one or more procedures selected from the group consisting of: (i) adjusting the front pad absorbency under load (AUL) to a value of about 23 grams of fluid/gram of material or more; (ii) adjusting the percent utilization of the absorbent core (MS100) to a value of about 43% or more; (iii) adjusting the surrounds efficiency (Se) to a value of about 90% or more; (iv) adjusting the third void strikethrough (St) to a value of less than about 30 seconds; and (v) maintaining the total capacity of the absorbent article (Tc) to a value of less than about 495 grams and greater than about 465 grams.

32. The method of claim 31, wherein the front pad absorbency under load (AUL) is adjusted to a value greater than 23.5.

33. The method of claim 32, wherein the front pad absorbency under load (AUL) is adjusted to a value greater than 24.

34. The method of claim 31, wherein the percent utilization (MS100) of the absorbent core is adjusted to greater than about 43.5%.

35. The method of claim 34, wherein the percent utilization (MS100) of the absorbent core is adjusted to greater than about 44.5%.

36. The method of claim 31, wherein the total capacity Tc is maintained at a value within the range of from about 465 grams to about 490 grams.

37. The method of claim 31, wherein the total capacity Tc is maintained at a value within the range of from about 465 to about 485.

38. The method of claim 31, wherein the third void strikethrough (St) of the absorbent article is adjusted to be less than about 28 seconds.

39. The method of claim 38, wherein the third void strikethrough (St) of the absorbent article is adjusted to be less than about 27 seconds.

40. The method of claim 31, wherein the surrounds efficiency (Se) is adjusted to be greater than about 93%.

41. The method of claim 40, wherein the surrounds efficiency (Se) is adjusted to be greater than about 94%.

42. The method of claim 31, wherein at least two of the procedures are carried out.

43. The method of claim 31, wherein all of the procedures are carried out.

44. A method of designing an absorbent article to have reduced overall leakage comprising modifying one or more absorbent article variables by carrying out one or more procedures selected from the group consisting of: (i) adjusting the front pad absorbency under load (AUL) to a value of about 23 grams of fluid/gram of material or more; (ii) adjusting the percent utilization of the absorbent core (MS100) to a value of about 43% or more; (iii) adjusting the surrounds efficiency (Se) to a value of about 89% or more; (iv) adjusting the third void strikethrough (St) to a value of less than about 38 seconds; and (v) maintaining the total capacity of the absorbent article (Tc) to a value of less than about 495 grams and more than about 465 grams.

45. The method of claim 44, wherein the front pad absorbency under load (AUL) is adjusted to a value greater than 23.5.

46. The method of claim 45, wherein the front pad absorbency under load (AUL) is adjusted to a value greater than 24.

47. The method of claim 44, wherein the percent utilization (MS100) of the absorbent core is adjusted to greater than about 43.5%.

48. The method of claim 47, wherein the percent utilization (MS100) of the absorbent core is adjusted to greater than about 44.5%.

49. The method of claim 44, wherein the total capacity Tc is maintained at a value within the range of from about 465 grams to about 490 grams.

50. The method of claim 44, wherein the total capacity Tc is maintained at a value within the range of from about 465 to about 485.

51. The method of claim 44, wherein the third void strikethrough (St) of the absorbent article is adjusted to be less than about 35 seconds.

52. The method of claim 51, wherein the third void strikethrough (St) of the absorbent article is adjusted to be less than about 28 seconds.

53. The method of claim 44, wherein the surrounds efficiency (Se) is adjusted to be greater than about 93%.

54. The method of claim 53, wherein the surrounds efficiency (Se) is adjusted to be greater than about 94%.

55. The method of claim 44, wherein at least two of the procedures are carried out.

56. The method of claim 44, wherein all of the procedures are carried out.

57. A method of making the absorbent article of claim 1 comprising providing a top sheet, a back sheet, and an absorbent core to a garment forming station; and disposing the absorbent core between the top sheet and the back sheet at the garment forming station to form the absorbent article.

58. The method of claim 57, wherein the 3 variable urine only leakage performance index ($PI_{3UL}$) is less than about 2.9.

59. The method of claim 57, wherein the 3 variable urine only leakage performance index ($PI_{3UL}$) is less than about 2.7.

60. The absorbent article of claim 57, wherein the 3 variable urine only leakage performance index ($PI_{3UL}$) is within the range of from about 0.5 to about 2.9.

61. The absorbent article of claim 57, wherein the 3 variable urine only leakage performance index ($PI_{3UL}$) is within the range of from about 0.75 to about 2.7.

62. The absorbent article of claim 57, wherein the absorbent article is a Stage 4 diaper.

63. A method of determining the three variable urine only leakage performance index of an absorbent article comprising:

measuring at least the total capacity, the front pad AUL and the percent utilization of the absorbent article;

optionally measuring the surrounds efficiency and the third void strikethrough of the absorbent article; and calculating the three variable urine only leakage performance index of the article by carrying out the following calculation (1):

$$PI_{3UL}=0.046(Tc)-2.94(MS1-00)-0.772(AUL) \quad (1)$$

where Tc is the total capacity in grams, MS100 is the percent utilization of the absorbent core upon insult with 100 ml of 0.9 wt % saline solution, and AUL is the front pad absorbency under load of the absorbent article, expressed in grams of 0.9 wt % saline solution absorbed per gram of pad material, the AUL having a value of about 23 grams of fluid/gram of material or more.

64. A method of determining the five variable urine only leakage Performance Index comprising:

measuring at least the total capacity, the front pad AUL, the percent utilization, the surrounds efficiency, and the third void strikethrough of the absorbent article;

and calculating the five variable urine only leakage performance index of the article by carrying out the following calculation (2):

$$PI_{5UL}=0.006(Tc)-7.094(Se-)+1.108(MS100)-0.18(AUL)+0.023(St) \quad (2)$$

where Se is surrounds efficiency, St is the third void strikethrough, Tc is the total capacity of the article in grams, MS100 is the percent utilization of the core upon insult with 100 ml of 0.9 wt % saline solution, and AUL is the front pad absorbency under load of the absorbent article, expressed in grams of 0.9 wt % saline solution absorbed per gram of pad material, the AUL having a value of about 23 grams of fluid/gram of material or more.

65. A method of designing an absorbent article having reduced leakage comprising:

measuring a plurality of variables on a plurality of different absorbent articles;

determining through use testing the percentage of the plurality of absorbent articles that have urine only leakage, and that have overall leakage;

determining through regression analysis which of the plurality of variables for the plurality of absorbent articles provides a substantially direct correlation with the urine only leakage percentage and/or overall leakage percentage to produce at least two leakage variables that substantially directly correlate with leakage percentage; and determining through regression analysis a direct correlation between a combination of the at least two leakage variables and urine only leakage and/or overall leakage to provide a multi-variable performance index; and adjusting the multi-variable performance index to reduce the leakage percentage of the absorbent article.

* * * * *